US011695975B1

(12) United States Patent
Giraud

(10) Patent No.: US 11,695,975 B1
(45) Date of Patent: Jul. 4, 2023

(54) SYSTEM AND METHOD FOR LIVE WEB CAMERA FEED AND STREAMING TRANSMISSION WITH DEFINITIVE ONLINE IDENTITY VERIFICATION FOR PREVENTION OF SYNTHETIC VIDEO AND PHOTOGRAPHIC IMAGES

(71) Applicant: Stephen G. Giraud, Petaluma, CA (US)

(72) Inventor: Stephen G. Giraud, Petaluma, CA (US)

( * ) Notice: Subject to any disclaimer, the term of this patent is extended or adjusted under 35 U.S.C. 154(b) by 175 days.

(21) Appl. No.: 17/194,011

(22) Filed: Mar. 5, 2021

Related U.S. Application Data

(60) Provisional application No. 62/986,675, filed on Mar. 7, 2020.

(51) Int. Cl.
| | |
|---|---|
| *H04N 21/475* | (2011.01) |
| *G06V 40/00* | (2022.01) |
| *G06F 21/31* | (2013.01) |
| *H04W 12/08* | (2021.01) |
| *G16Y 40/00* | (2020.01) |

(Continued)

(52) U.S. Cl.
CPC ... *H04N 21/25875* (2013.01); *A61B 5/02055* (2013.01); *A61B 5/117* (2013.01); *G06V 40/1365* (2022.01); *G06V 40/172* (2022.01); *G06V 40/40* (2022.01); *H04N 21/2187* (2013.01); *H04N 21/2407* (2013.01);

(Continued)

(58) Field of Classification Search
CPC ......... H04N 21/25875; H04N 21/2187; H04N 21/2407; A61B 5/02055; A61B 5/117; A61B 5/024; A61B 5/0816; A61B 2562/0271; G06V 40/1365; G06V 40/172; G06V 40/40; G06V 30/10
See application file for complete search history.

(56) References Cited

U.S. PATENT DOCUMENTS

| | | |
|---|---|---|
| 5,960,081 A | 9/1999 | Vynne et al. |
| 6,633,651 B1 | 10/2003 | Hirzalla et al. |

(Continued)

*Primary Examiner* — Alazar Tilahun
(74) *Attorney, Agent, or Firm* — Robert Cantrell; Jose W. Jimenez; Jimenez Law Firm

(57) ABSTRACT

A live web camera feed and streaming transmission system and method for gathering, identifying and authenticating biometric data of a specific human being while constantly monitoring, tracking, analyzing, storing and distributing dynamic biometric data to ensure authorized access to the secured system continues via positive live feed monitoring of biometric data for participating computer systems and or programs. Multiple, correlative, inseparable, embedded serial numbers allow for editing within a live video recording session because the serial numbers are "attached" to one another from frame to frame. The degree of identity verification correlated with the various serial numbers, directly affects an indelible, detectible, identity verification cumulative authentication rating score in conjunction with a recognizable and standardized, indelible, detectible, hyperlinked color-coded security badge displaying the degree of identity authentication. If any one of these components that work cooperatively and correlatively is tampered with in any regard, the video is rendered inoperable.

18 Claims, 10 Drawing Sheets

(51) Int. Cl.
　　　*H04N 21/258*　　(2011.01)
　　　*A61B 5/117*　　(2016.01)
　　　*H04N 21/2187*　　(2011.01)
　　　*H04N 21/24*　　(2011.01)
　　　*A61B 5/0205*　　(2006.01)
　　　*G06V 40/40*　　(2022.01)
　　　*G06V 40/16*　　(2022.01)
　　　*G06V 40/12*　　(2022.01)
　　　*A61B 5/024*　　(2006.01)
　　　*A61B 5/08*　　(2006.01)
　　　*G06V 30/10*　　(2022.01)

(52) U.S. Cl.
　　　CPC ............ *A61B 5/024* (2013.01); *A61B 5/0816* (2013.01); *A61B 2562/0271* (2013.01); *G06V 30/10* (2022.01)

(56) References Cited

U.S. PATENT DOCUMENTS

| | | |
|---|---|---|
| 7,216,232 B1 | 5/2007 | Cox et al. |
| 7,793,318 B2 | 9/2010 | Deng |
| 10,552,667 B1 | 2/2020 | Bogan, III et al. |
| 10,693,872 B1 * | 6/2020 | Larson .................... G06F 21/31 |
| 10,810,725 B1 * | 10/2020 | Dolhansky .............. G06N 3/084 |
| 2002/0184538 A1 * | 12/2002 | Sugimura ................ G06F 21/32 |
| | | 726/5 |
| 2006/0047967 A1 | 3/2006 | Akhan et al. |
| 2007/0083815 A1 | 4/2007 | Delorme et al. |
| 2008/0002894 A1 | 1/2008 | Hayon et al. |
| 2009/0290752 A1 | 11/2009 | Kalva |
| 2010/0177891 A1 | 7/2010 | Keidar et al. |
| 2013/0102283 A1 * | 4/2013 | Lau .................... G06Q 30/0269 |
| | | 455/411 |
| 2014/0325550 A1 | 10/2014 | Winograd et al. |
| 2014/0330729 A1 * | 11/2014 | Colangelo .......... G06Q 20/4012 |
| | | 705/72 |
| 2016/0239657 A1 * | 8/2016 | Loughlin-McHugh ...................... G06F 21/45 |
| 2017/0214688 A1 * | 7/2017 | Potash ................ H04L 63/0861 |
| 2018/0189561 A1 * | 7/2018 | Bertan ................... G06V 40/70 |
| 2020/0065526 A1 | 2/2020 | Berman |

\* cited by examiner

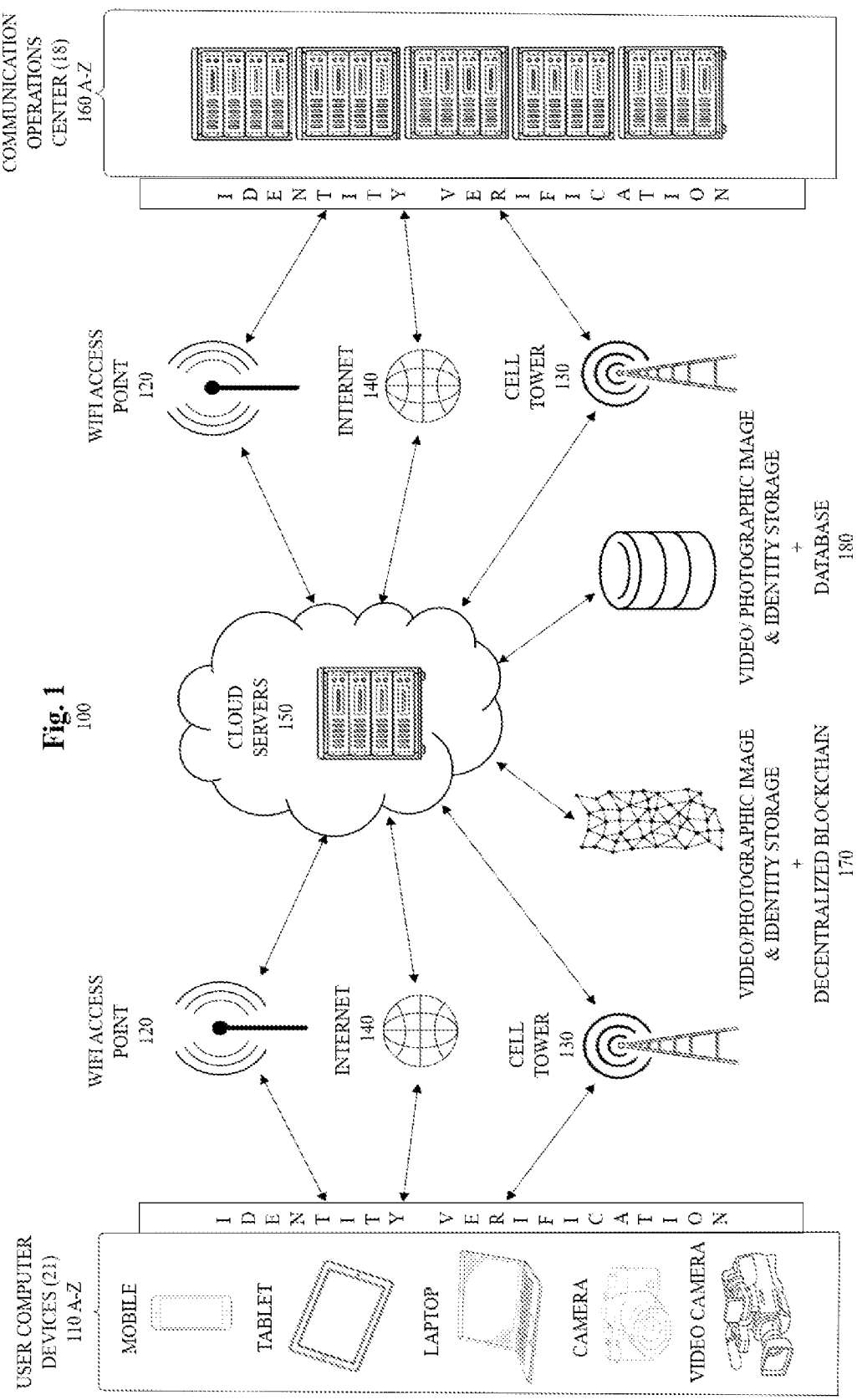

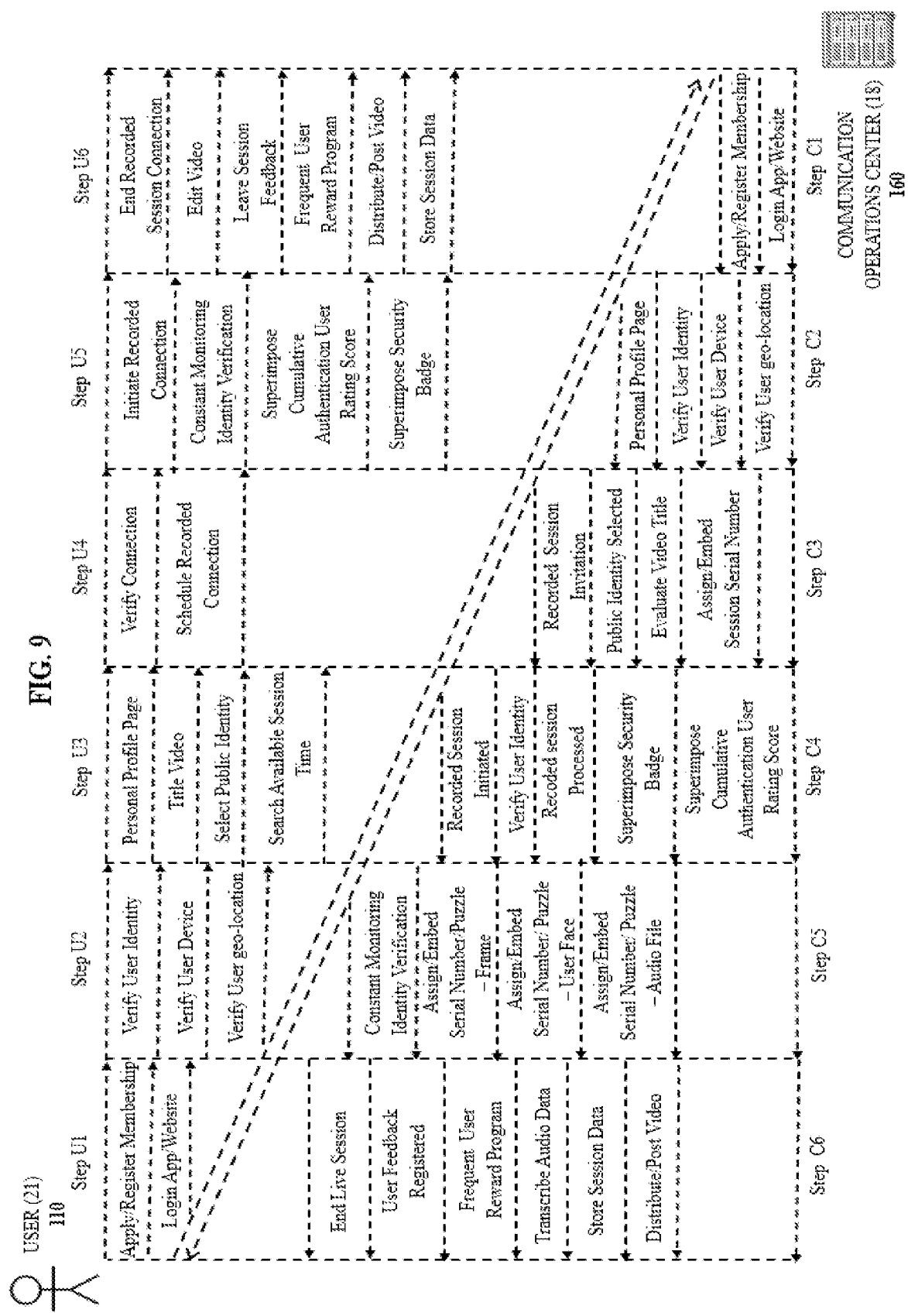

SYSTEM AND METHOD FOR LIVE WEB CAMERA FEED AND STREAMING TRANSMISSION WITH DEFINITIVE ONLINE IDENTITY VERIFICATION FOR PREVENTION OF SYNTHETIC VIDEO AND PHOTOGRAPHIC IMAGES

CROSS REFERENCE TO RELATED APPLICATION

This application claims priority of U.S. Provisional Application Ser. No. 62/986,675, filed Mar. 7, 2020.

BACKGROUND OF THE INVENTION

1. Field of the Invention

The present invention relates generally to government verified authentication systems and impregnable live video transmission communication networks for individual users. More particularly, the present invention is directed to a system and method for live web camera feed and streaming transmission with definitive online identity verification for prevention of synthetic video and photographic images for commercial and consumer clients.

2. Background Art

The conventional approach to massive-scale interaction of live video transmission communication system networks would be to develop a one-way video recording communication with a unique combination of both live video and audio transmission which allows full simplex communication between the sender and the receiver with the help of dedicated software and hardware. Such designs involve huge amounts of data transfer and are not reliably sustainable or scalable with regard to definitive real-time online identity verification solutions for individual users. Bandwidth requisites for recovery and authentic verification operations utilizing tremendous amounts of data from a central data repository would be enormous. Additionally, retrieval reaction times from a central data repository would be excessive. Finally, centralized solutions are susceptible to a number of potential security risks such as fire brigade attacks, spoofing attacks, and social engineering vulnerabilities.

Although live web camera feed and streaming transmission methods and systems are known, one vulnerability that persists in the industry is the lack of verified and verifiable authentication of the audio, video and photographic image recording with identity of a specific human being while accessing and participating in live web camera feed and streaming transmission systems. Known live web camera feed and streaming transmission methods and systems do not verify the authentication of a specifically identified human being via constant dynamic monitoring of positive, live feed and streaming transmissions, biometric data nor do they verify said identities via appropriate governmental agencies having performed due diligence on proof of life identification.

Also, once a specific individual user has been identified with the aid of biometric verification markers and has been granted access to a secure live web camera feed and streaming transmission system, constant dynamic monitoring of biometric data correlated with uniquely pertinent personal biographic information and geo-location coordinates is required to ensure that an authorized user has not exited the system, leaving an opportunity for non-authorized individual users to access the secure live web camera feed and streaming transmission system and unauthorized manipulation and or unauthorized editing of the recorded media.

Although the live web camera feed and streaming transmission industry is aware of this, current methods for securely gathering, identifying, authenticating and registering uniquely specific individual user data are imprecise at best. There too, is a perception amongst users that their privacy is being violated by the collection of biometric data for verification purposes causing justifiable concern about potential vulnerability to identity theft.

There is a need for a system and method for users to register their biometric data while concurrently addressing the privacy concerns to maintain public anonymity by enabling users to operate under an alias and or avatar, in exchange for increased identity security, governing terms of service, accurate rating systems with user feedback and offers of incentives such as commercial discounts, commercial coupons or frequent user rewards, contributing to and governing the systems terms of service and end user agreement. In addition, there is a lack of ubiquity in providing a registered individual user from using multiple registered cameras and computer devices as they move throughout the mobile society. There is a need for live web camera feed and streaming transmission systems to interface dynamically with specific markets, including but not limited to multiple types of identity fraud prevention, authentic marketing and research campaigns, e-commerce, workplace enforcement, government program and intelligence utilization, and regulatory/law enforcement, to name just a few.

There also exists a need for a live web camera feed and streaming transmission system and method for business to business (B2B), consumer to business (C2B) and or consumer to consumer (C2C) commercial market applications that securely gathers, identifies, authenticates and registers uniquely specific individual user biometric markers correlated with uniquely pertinent personal biographic information and geo-location coordinates that constantly monitors, tracks, analyzes, stores and distributes encrypted dynamic individual user data of a specific human being to provide authenticated audio, video and photographic image recordings for commercial and consumer clients.

SUMMARY OF THE INVENTION

The present invention overcomes the aforementioned problems and is distinguished over the prior art in general, by a system and method for live web camera feed and streaming transmission method that provides, through an app and website, authentic audio, video and photographic images utilizing individual identity verification for commercial and consumer clients with authentication based on definitive real-time identity verification of a specific human being using various registered Internet connected web style cameras utilizing microphones and thumbprint scanners within wired and or wireless computing communication devices such as mobile phones, tablets and any other Web network, or PC connected to the Internet utilizing microphones, thumbprint scanners and speakers to interface between the systems servers and networked computer systems for securely gathering, identifying, authenticating and registering individual user biometric markers correlated with uniquely pertinent personal biographic information while monitoring, tracking, analyzing, storing and distributing authenticated dynamic user security badge data including encrypted indelibly embedded session serial numbers correlated with encrypted indelibly embedded sequential serial numbers and geo-location coordinates within the specifically identified individuals face, the audio file within each recorded frame and an indelible detectable identity verification cumulative authentication rating score for identity fraud prevention, authentic marketing and research campaigns, e-commerce, workplace enforcement, government program and intelligence utilization, and regulatory/law enforcement markets.

In one embodiment, the invention may be implemented as a commercial identification system suitable for billions of individual users where each individual user is provided with a Unique Identification Number (UIN) in order to improve the provisioning of authorized commercial and independent authentication of original video and photographic images of verified individuals for a commercial and consumer client's security.

In another embodiment, the present invention is directed to business to business (B2B), business to consumer (B2C) and consumer to consumer (C2C) commercial market models envisioned within the system. The B2B, B2C and C2C commercial models comprise a unique human being having their identity verified based on an authentically issued government form of identification. As the live video and photographic images are transmitted and recorded in real-time to the systems website, a corresponding indelible, detectible, hyperlinked color-coded identity verification security badge operating simultaneously, cooperatively and correlatively with an indelible, detectable identity verification cumulative authentication rating score between 0%-100% is embedded and displayed for permanent record on a predetermined video and photographic image frame.

In another embodiment, the present invention is directed toward a method of gathering, identifying, authenticating and registering individual user biometric markers correlated with uniquely pertinent personal biographic information and geo-location coordinates. The method includes the steps of gathering a sufficient amount of biometric information directly from an individual user to uniquely identify the individual user through one or more or a plurality of OEM biometric detection and collection device(s) that interface(s) with wired and or wireless computing communication devices such as mobile phones, tablets, smart watches, gaming devices and any other Web network, or PC connected to the Internet utilizing microphones, thumbprint scanners, speakers and various style web cameras, along with uniquely pertinent personal biographic information of the individual user and geo-location coordinates and directing the user security badge data to the systems servers known as a communications manager and archive manger within a communication operations center then directing the data to a data group and its data group manager which stores the gathered biometric information at a randomly selected data bank having a plurality of data banks within the database, wherein the storing step includes randomly selecting the data bank based on the uniquely pertinent personal biographic information and geo-location coordinates gathered from the individual user.

In another embodiment, the present invention is directed toward a system for gathering, identifying, authenticating and registering individual user biometric information. The system includes one or more or a plurality of OEM biometric detection and collection device(s) that interface(s) with wired and or wireless computing communication devices such as mobile phones, tablets, smart watches, gaming devices and any other Web network, or PC connected to the Internet utilizing microphones, thumbprint scanners, speakers and various style web cameras and a data group manager. The one or more or a plurality of OEM biometric detection and collection device(s) interface with wired and or wireless computing communication devices such as mobile phones, tablets, smart watches, gaming devices and any other Web network, or PC connected to the Internet utilizing microphones, thumbprint scanners, speakers and various style web cameras for gathering a sufficient amount of biometric markers directly from an individual user to uniquely verify the individual users identity along with uniquely pertinent personal biographic information and geo-location coordinates of the individual user. The system is directed to a method of then monitoring, tracking, analyzing, storing and distributing dynamic individual user data of a specific human being for commercial endeavors via wired and or wireless computing communication devices such as mobile phones, tablets, smart watches, gaming devices and any other Web network, or PC connected to the Internet utilizing microphones, thumbprint scanners, speakers and various style web cameras. The data group manager separately stores the gathered biometric information along with uniquely pertinent personal biographic information of the individual user and geo-location coordinates at a randomly selected data bank in a biometric verification and data management system having a plurality of data banks at multiple levels of the data management system. The data group manager randomly selects the data bank based on the uniquely pertinent personal biographic information and geo-location coordinates gathered from the individual user.

In another embodiment, the present invention is directed toward OEM biometric detection and collection device(s) that interface with wired and or wireless computing communication devices such as mobile phones, tablets, smart watches, gaming devices and any other Web network, or PC connected to the Internet utilizing microphones, thumbprint scanners, speakers and various style web cameras for gathering pertinent personal biographic information and geo-location coordinates. The OEM biometric detection and collection device(s) include a biometric data input mechanism for gathering a sufficient amount of biometric markers directly from an individual user to uniquely identify the individual user; which interfaces with wired and or wireless computing communication devices such as mobile phones, tablets, smart watches, gaming devices and any other Web network, or PC connected to the Internet utilizing microphones, thumbprint scanners, speakers and various style web cameras for gathering the biometric markers, pertinent personal biographic information and geo-location coordinates from the individual user for transmitting the gathered biometric markers, pertinent personal biographic information and geo-location coordinates over a wired or wired and or wireless connection to an external database (biometric verification and data management system) or decentralized blockchain, government agency and commercial distribution channels when the wired and or wireless connection is available. The wired and or wireless computing communication devices such as mobile phones, tablets, smart watches, gaming devices and any other Web network, or PC connected to the Internet utilizing microphones, thumbprint scanners, speakers and various style web cameras also includes within the systems servers an internal data storage mechanism for storing the gathered biometric markers, pertinent personal biographic information and geo-location coordinates when the wired and wireless connection is not available; and a network interface controller for detecting when the wired and or wireless connection is available, and for controlling the transmitter and the internal data storage mechanism.

When the wired and or wireless connection becomes available and biometric markers, uniquely pertinent personal biographic information, geo-location coordinates and live web camera feed and stream transmission recorded session data are stored in the internal data storage mechanism, the network interface controller causes the transmitter to automatically transmit the biometric markers, gathered uniquely pertinent personal biographic information, geo-location coordinates and live web camera feed and streaming transmission recorded session data to the external database (biometric verification and data management system) or decentralized blockchain.

In another embodiment, the present invention is directed toward OEM biometric detection and collection device(s) that interface with wired and or wireless computing communication devices such as mobile phones, tablets, smart watches, gaming devices and any other Web network, or PC connected to the Internet utilizing microphones, thumbprint scanners, speakers and various style web cameras for gathering pertinent personal biographic information and geo-location coordinates. The OEM biometric detection and collection device(s) include a biometric data input mechanism for gathering a sufficient amount of biometric markers directly from an individual user to uniquely identify the individual user; which interfaces with wired and or wireless computing communication devices such as mobile phones, tablets, smart watches, gaming devices and any other Web network, or PC connected to the Internet utilizing microphones, thumbprint scanners, speakers and various style web cameras for gathering the biometric markers, pertinent personal biographic information and geo-location coordinates from the individual user for transmitting the gathered biometric markers, pertinent personal biographic information and geo-location coordinates over a wired or wired and or wireless connection to an external database (biometric verification and data management system) or decentralized blockchain, government agency and commercial distribution channels when the wired and or wireless connection is available.

The wired and or wireless computing communication devices such as mobile phones, tablets, smart watches, gaming devices and any other Web network, or PC connected to the Internet utilizing microphones, thumbprint scanners, speakers and various style web cameras also includes within the system's servers an internal data storage mechanism for storing the gathered biometric markers, pertinent personal biographic information and geo-location coordinates when the wired and or wireless connection is not available; and a network interface controller for detecting when the wired and or wireless connection is available, and for controlling the transmitter and the internal data storage mechanism.

When the wired and or wireless connection becomes available and biometric markers, uniquely pertinent personal biographic information, geo-location coordinates and live web camera feed and streaming transmission recorded session data are stored in the internal data storage mechanism, the network interface controller causes the transmitter to automatically transmit the biometric markers, gathered uniquely pertinent personal biographic information, geo-location coordinates and live web camera feed and streaming transmission recorded session data including a user's indelible, detectable identity verification cumulative authentication rating score between 0%-100%, a displayed, hyperlinked, indelible, detectable security badge that may be clicked by a viewer to verify media data authenticity (transcribed audio files, date/time/geo-location, etc.) through the systems servers and embedded, indelible, encrypted, undetectable session serial numbers, facial serial numbers, voice print (audio file) serial numbers and video frame serial numbers, to the external database (biometric verification and data management system) or decentralized blockchain.

Other differences and advantages of the invention will become apparent from time to time throughout the specification and claims as hereinafter related.

BRIEF DESCRIPTION OF THE DRAWINGS

The following section describes the present invention with reference to exemplary embodiments illustrated in the figures, in which:

FIG. 1 is a block diagram that depicts an example of the system architecture, according to an embodiment of the invention;

FIG. 9 is a bi-directional sequence diagram that depicts a sequence of steps that are performed by the different elements within FIG. 1 through FIG. 8 according to an embodiment of the invention.

GLOSSARY OF TERMS

Figure 2A:
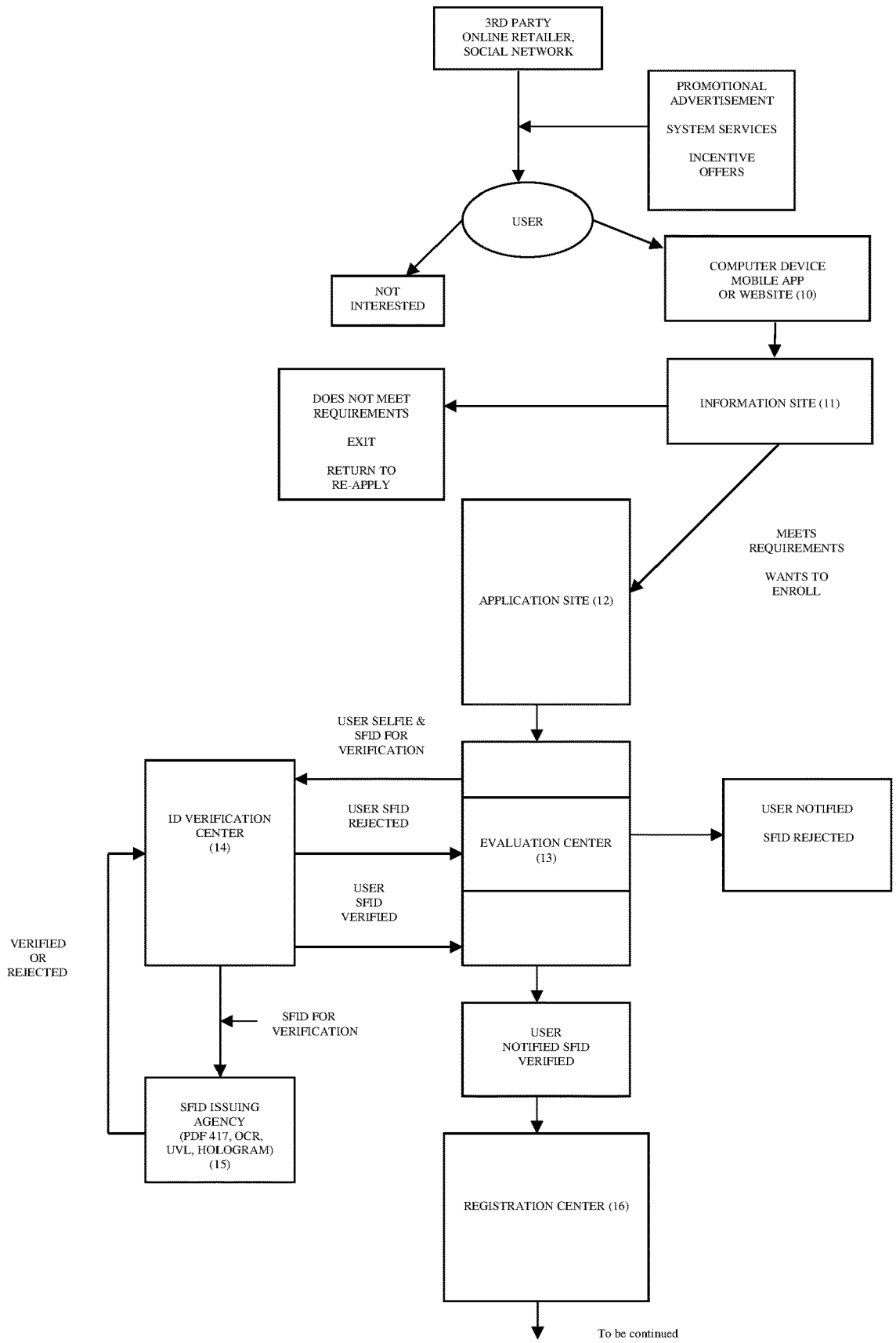
FIG. 2A and FIG. 2B taken together is a flow chart illustrating the steps of an exemplary embodiment of a method of the present invention when utilized for applying and registering for access to an identity verification system for authenticating biometric markers of a specific human being correlated with pertinent personal biographic information and geo-location coordinates granting authorized access to live web camera feed and streaming transmissions of video and photographic images.

As used in conjunction with the present invention, the following terms have the following meanings.

The term "synthetic video and photographic images" means synthetic media in which a person in an existing image or video is replaced with fake content with a high potential to deceive, also known as "deepfake" or "deep fake".

The term "B2B" means Business to Business. A "B2B" type of business model is suitable for companies that facilitate the transaction of products and or services to another company, which in this example is the final client who then utilizes the product and or service. The term "B2C" means Business to Consumer. A "B2C" type of business model is suitable for companies that facilitate the transaction of products and or services to a consumer, which in this example is the final client who then utilizes the product and or service. The term "C2C" means Consumer to Consumer. A "C2C" type of business model facilitates the transaction of products and or services between consumers and gives an opportunity to sell or purchase goods and or services directly with each consumer as a potential final client.

The term "subscriber client" means any final client who facilitates the transaction of and utilizes the product and or service as described within the system. The term "user" or "users" means registered camera operators and or registered content providers which may comprise actors, models, posers, and/or a cast of characters.

The term "session" or sessions" means a state of elapsed time that is preserved between both a user and the Communication Operations Center (COC) within a scheduled request initiated by a user and accepted by the Communication Operations Center. In an embodiment, a session is created by scheduling a live web camera feed and streaming transmission within the system of the present invention. A new session may be created on the scheduling request by a user to the Communication Operations Center (COC). A session must be authorized by both a user and the Communication Operations Center to enable access to a live web camera feed and streaming transmission within the system of invention. Within a session, any contents of a live web camera feed and streaming transmission may be recorded between both a user and the Communication Operations Center. The request to initiate a live web camera feed and streaming transmission from a registered user and device may be used to schedule many sessions from a user to the Communication Operations Center simultaneously. Sessions are stored in the system's distributed Data Banks (DB's), an external data base or decentralized blockchain. The term "blockchain" means a data structure that holds transactional records and while ensuring security, transparency, and decentralization. A subscriber client that requests stored sessions may contact the system of the present invention, which performs a local fetch from a queue or performs a remote fetch by sending a request to either an external data base or decentralized blockchain. An Advanced Message Queuing Protocol (AMQP) server may be used as a common bus for session distribution: an object change event is broadcasted to all data bases or decentralized blockchain instances, consumed by the appropriate live web camera feed and steaming transmissions processed, and distributed to session queues.

DETAILED DESCRIPTION OF THE INVENTION

Referring now to the drawings by numerals of reference, there is shown in FIG. 1, a block diagram that depicts an example of the system architecture 100, according to an embodiment of the invention. System architecture 100 comprises user computer devices 110 A-Z utilizing identity verification, a Wi-Fi access point 120, a cell tower 130, the Internet 140, Cloud Server 150, Communication Operations Center (18) 160 A-Z utilizing identity verification, with decentralized blockchain 170 and a database 180 for storing user identity and live web camera feed and streaming transmission data. The Communication Operations Center (18) 160 A-Z utilizing identity verification executes software that enables user computer devices 110 A-Z utilizing identity verification to transmit real-time live stream push notifications from Cloud Server 150 and receive a live web camera feed and streaming transmission (i.e., in real-time) from another intermediary associated with Cloud Server 150. System architecture 100, particularly Cloud Server 150, allows different types of live media uploading such as: registered tablet-to-communication operations center, laptop-to-communication operations center, camera-to-communication operations center and video camera-to-communication operations center. The user that operates computer device 110 A-Z utilizing identity verification is referred to herein as the "user". As indicated above, computer device 110 A-Z utilizing identity verification may be referred to as a "user computer device."

User computer device 110 A-Z utilizing identity verification captures images and generates a live web camera feed and streaming transmission from the captured images. User computer device 110 A-Z utilizing identity verification executes a software application that establishes a communication channel with Cloud Server 150 in order to send the live web camera feed and streaming transmission (and an indication thereof) to Cloud Server 150. The application causes metadata about the live web camera feed and streaming transmission e.g., information about the user of user computer device 110 A-Z, utilizing identity verification information about user computer device 110 A-Z utilizing identity verification and a title for the live web camera feed and streaming transmission session data, geo-location of user computer device 110 A-Z utilizing identity verification, to be sent along with the live web camera feed and streaming transmission.

Non-limiting examples of user computer devices 110 A-Z utilizing identity verification include a wired and or wireless computing communication device such as mobile phones, tablets, smart watches, gaming devices and any other Web network, or PC connected to the Internet utilizing microphones, thumbprint scanners, speakers and various style web cameras that includes a video and or audio recorder.

Audio, video and photographic image streams from user computer devices 110 A-Z utilizing identity verification are assigned and embedded a cooperative and correlative session serial number (SSN), a user security badge (USB), a cumulative user rating score (URS), a frame serial number (FRSN), a facial serial number (FASN), and an audio serial number (ASN) that are all interdependent of each other, then processed, stored, transcoded, transcribed and prepared for live consumption or recordings by software and hardware components (not shown) associated through Cloud Server 150 by Communication Operations Center (18) 160 A-Z. Metadata about a live web camera feed and streaming transmission from user computer devices 110 A-Z utilizing identity verification is also processed and stored in a DB. Metadata about a live web camera feed and streaming transmission session may be updated continuously within a personal profile page of users, such as the duration of a live web camera feed and streaming transmission session, the loss of a connection, reconnection, for users of a registered computer device, or the monetary incrementing from the user's computer device that is contained within an e-wallet.

User Computer device 110 A-Z utilizing identity verification is communicatively coupled to Cloud Server 150 via an optional Wi-Fi access point 120 or cell tower 130 and Internet 140. Similarly, Communication Operations Center (18) 160 A-Z utilizing identity verification are communicatively coupled to Cloud Server 150 via an optional Wi-Fi access point 120 or cell tower 130 and Internet 140.

Cloud Server 150 receives an indication of a live web camera feed and streaming transmission that is being transmitted (or is about to be transmitted) from User Computer device 110 A-Z utilizing identity verification. Cloud Server 150 sends real-time live stream push notifications of the live web camera feed and streaming transmission to Communication Operations Center (18) 160 A-Z utilizing identity verification, whose users have previously subscribed for the push notification. Components of Cloud Server 150 analyze changes in database tables and stores those changes for fast retrieval within a decentralized blockchain 170 and or a database 180.

As indicated above, the Communication Operations Center (18) 160 A-Z utilizing identity verification may be referred to as "COC". Any communication protocol that is necessary to transmit the live web camera feed and streaming transmission from Cloud Server 150 to the Communication Operations Center (18) 160 A-Z utilizing identity verification may be used.

The Communication Operations Center (18) 160 A-Z utilizing identity verification are any servers that are configured to receive a real-time live stream push notification of live web camera feed and streaming transmission from Cloud Server 150. As shown in FIG. 1, non-limiting examples of the Communication Operations Center (18) 160 A-Z utilizing identity verification include: File Servers, Network Servers e.g. Local Area Network, Wide Area Network (WAN) each executing software that enables the server to receive real-time live stream push notifications from Cloud Server 150. Additionally, or alternatively, the Communication Operations Center (18) 160 A-Z utilizing identity verification may transmit an email or SMS message that notifies the User Computer devices 110 A-Z utilizing identity verification that a live web camera feed and streaming transmission is ready to receive. The users then have to use a web browser application or app software that enables the users to initiate the live web camera feed and streaming transmission from their respective devices.

If a User Computer device 110 A-Z is a PC, such as a laptop or desktop computer, then the live web camera feed and streaming transmission may be transcoded to a Flash format (e.g., Flash file formats FLV or F4V) and then delivered to the Communication Operations Center (18) 160 A-Z. If a User Computer device 110 A-Z is a mobile device, then the live web camera feed and streaming transmission may be transcoded into a format that is supported by the mobile device and then transmitted to the Communication Operations Center (18) 160 A-Z.

A real-time live stream push notification of a live web camera feed and streaming transmission may be sent to the Communication Operations Center (18) 160 A-Z utilizing identity verification prior to any portion of the live web camera feed and streaming transmission being sent to Communication Operations Center (18) 160 A-Z utilizing identity verification. Alternatively, the live web camera feed and streaming transmission and the real-time live stream push notification are sent contemporaneously to Communication Operations Center (18) 160 A-Z utilizing identity verification. In this case, the Communication Operations Center (18) 160 A-Z utilizing identity verification may display the real-time live stream push notification and at least a portion of the live web camera feed and streaming transmission simultaneously. The real-time live stream push notification provides an opportunity for the Communication Operations Center (18) 160 A-Z to immediately receive or reject the live web camera feed and streaming transmission.

A real-time live stream push notification may indicate any type of information about the user and or the live web camera feed and streaming transmission. For example: a real-time live stream push notification may indicate the legal name or alias of the user, the geo-location of the registered User Computer device, and or any data indicated by the registered User Computer device, such as a level of priority of the live web camera feed and streaming transmission or session title given to the live web camera feed and streaming transmission session. Additionally, a real-time live stream push notification may include a frame of video from the live web camera feed and streaming transmission displaying the user or any selected avatar to protect privacy. Additionally, or alternatively, the live web camera feed and streaming transmission may be automatically distributed or posted to one or more video or photographic image service platform without any input received from the one or more video or photographic image service platforms.

A potential video or photographic image service platform connects to Cloud Server 150 and specifies video or photographic image frames that are of interest to the viewer of the video or photographic image service platforms. For example, a potential viewer may provide: commercial data that indicates an area of interest in all future live web camera feed and streaming transmission sessions initiated by a potential user, live web camera feed and streaming transmissions whose corresponding title and or description includes a particular subject or priority, live web camera feed and streaming transmissions that are associated with a particular industry, live web camera feed and streaming transmissions that are produced in certain geo-locations or regions, and or live web camera feed and streaming transmissions that are produced during a particular and or available time period. Commercial data is stored in a database 180 and or decentralized blockchain 170.

The Communication Operations Center (18) 160 A-Z utilizing identity verification might execute an application (e.g., a web browser application) that is communicatively coupled to a particular service application. The service application may be part of, for example, a commercial or government website. Thus, for example, if a registered User's Computer device is currently logged into a commercial or government website, then Cloud Server 150 sends a real-time live stream push notification to the commercial or government website using the appropriate identity of the registered users and the registered Users Computer device. The commercial or government website then uses the commercial or government website identity of the registered user to send the real-time live stream push notification to the viewer's device, video or photographic image service platforms.

FIG. 2A and FIG. B taken together is a flow chart illustrating the steps of an exemplary embodiment of a method of the present invention when utilized for applying and registering for access to an online identity verification system for authenticating biometric markers of a specific human being correlated with pertinent personal biographic information and geo-location coordinates. An individual user is guided from the systems website and or app of invention incentive programs and or through third party promotion via a wired and or wireless computing communication device such as: mobile phones, tablets, smart watches, gaming devices and any other Web network, or PC connected to the Internet utilizing microphones, thumbprint scanners, speakers and various style web cameras that includes a video and or audio recorder 10. The individual user enters the information section of the website and or app of the system 11, is educated and incentivized as to the services and benefits of the system's use and on the registration requirements which requires a current state or federally issued form of Identification (SFID) such as: a driver's license, military, state identification, or passport. In the event that the applying individual user does not meet the requirements for registration, the individual user exits the system and will have the opportunity to re-apply.

In the event that the applying individual user does meet the requirements for registration, the individual user is guided into the application site of the systems website and or app 12 whereby the individual user is instructed to complete an online application and an associated questionnaire. The applying individual user is instructed to take a digital photograph of the applying individual user's current state or federally issued identification. The applying individual user displays his or hers identification within the cameras field of vision or scanning window as displayed on the individual users' computer or mobile computing communications device screen or by uploading the photograph from a separate registered camera device within the field of vision or scanning window as displayed on the individual users' computer or mobile computing communications device screen.

The next step in the application process is for the individual user to take his or her own digital photograph (selfie) and verify "liveness" based on blinking. The individual user is instructed to format his or her face within the provided displayed field of vision or scanning window of the registered camera as produced on the individual users' computer or mobile computing communications device screen and once the registered camera is in focus, blink the individual users' eyelids, capture the image, save, then upload the photograph of themselves and of the SFID along with the application to the application center within the system of invention.

Once the application and the photographs of the individual user (selfie) and of the state or federally issued identification are received within the evaluation center 13, the photographs are compared to one another in order to verify that the applying individual user matches the individual user displayed in the SFID through the analysis of biometric markers and complex biometric algorithms within the identification verification center 14. In the event that the authenticity of the individual user's SFID is rejected, then the individual user does not meet the requirements for registration within the evaluation center 13, the individual user will then exit the system of invention and will have the opportunity to re-apply.

In the event that the individual user's photograph of themselves (selfie) and of the SFID has been positively verified as identical by the identification verification center 14, the individual user's identification will be compared by, but not limited to a PD F417 two-dimensional high-density stacked linear barcode, capable of encoding text, files and data bytes, or similar, such as for example: Optical Character Recognition, Ultra Violet Lighting and Hologram detection that may contain biometric data and pertinent personal biographic information that is often included on a current and corresponding government issued state or federal identification (SFID) 15 for electronic authentication. In the event that the individual user's state or federally issued identification is rejected by the SFID issuing agency 15 as being invalid, then the individual user does not meet the requirements for the evaluation center 13, the individual user is notified of the rejection and is instructed to correct the invalid identification before re-applying.

In the event that the individual user's identification is authenticated through the SFID issuing agency 15, the individual user is notified of the SFID authentication then proceeds to the registration center 16. At this step in the process, the individual user is instructed to fill out and to submit pertinent personal biographic information, a marketing questionnaire for interest and preferences, select an alias and an avatar for public identification display if desired. In addition, the individual user is instructed to select any additional biometric detection and collection device(s) 22 as needed for future use within the system of invention as desired. The fulfillment of the biometric detection and collection device(s) 22 is made by the utilization center 17. Within the utilization center 17, biometric detection and collection devices 22, key codes for downloading the biometric telemetry software, instructions for installing the biometric detection and collection device(s) 22 and software along with customer support and contact information are provided if needed. The instructions direct individual users to log into the COC 18 to complete the final verification and initialization of service upon successful utilization of all biometric detection and collection device(s) 22 with corresponding software if needed. The individual user is then instructed to log into the system's COC to complete the registration process in order to initiate service.

The next step in the registration process is for the individual user to enter the presence verification portal (PVP) 19 where the system performs a presence and "liveness" verification based on facial recognition, blinking, voice and thumb print analysis or any other biometric marker in order to verify that the registering individual user is identical to the applying individual user. In the event that the presence verification fails, the individual user does not meet the requirements for the presence verification portal registration, the individual user contacts customer support and has the opportunity to re-register.

In the event that the individual user passes the presence verification portal, the individual user is guided into the system initialization portal (SIP) 20 where additional biometric markers correlated with pertinent personal data and geo-location coordinates via biometric detection and collection device(s) may be gathered and processed. The SIP 20 then issues a unique identification number (UIN) to the registering individual user to be used within the live web camera feed and streaming transmission system. Upon issuance of the UIN, the individual user has achieved a successful service initialization and is now authorized for live web camera feed and streaming transmissions, recordings and full public system access.

Figure 2B:
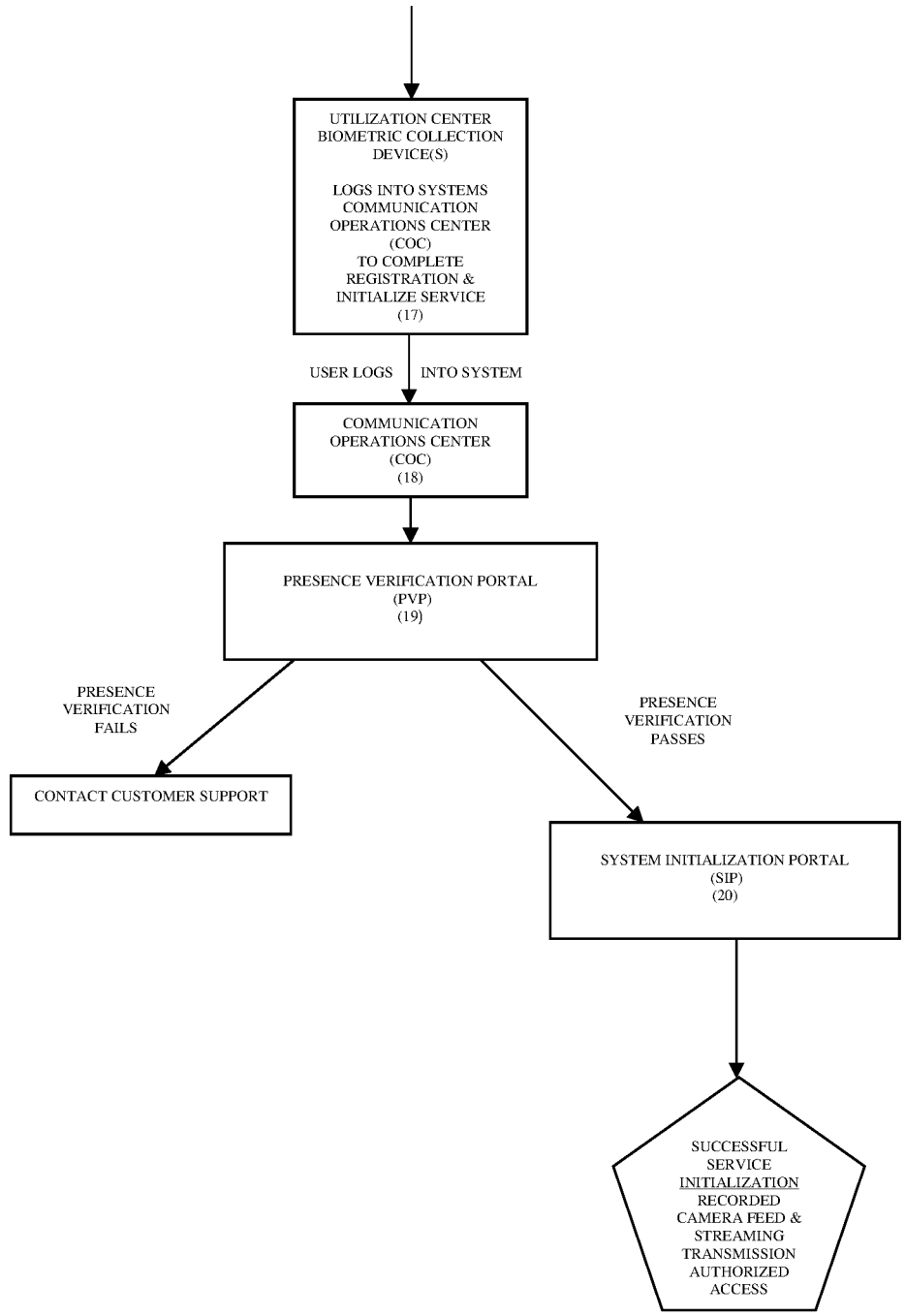
Figure 3:
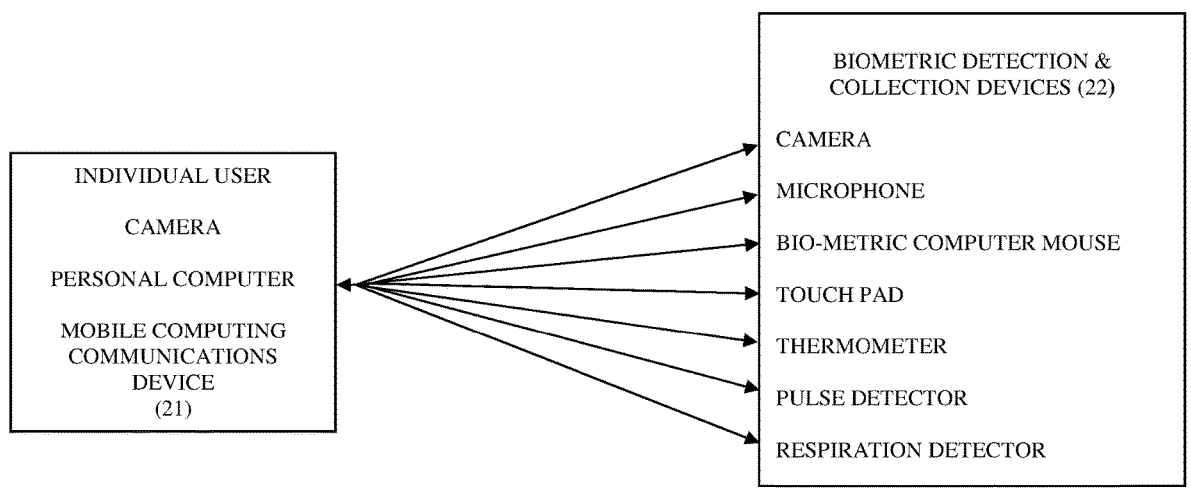
FIG. 3 is a simplified block diagram of an exemplary embodiment of a registered OEM biometric detection and collection device interfacing with an individual users' wired and or wireless computing communication devices such as mobile phone, tablet, smart watch, gaming device and any other Web network, or PC connected to the Internet utilizing microphones, thumbprint scanners, speakers and various style web cameras.

FIG. 3 is a simplified block diagram of an exemplary embodiment of an OEM biometric detection and collection device interfacing with wired and or wireless computing communication devices such as: mobile phones, tablets, smart watches, gaming devices and any other Web network, or PC connected to the Internet utilizing microphones, thumbprint scanners, speakers and various style web cameras of an individual user. As shown in FIG. 2B, the biometric collection device(s) utilization center 17, directs the user to utilize the biometric detection and collection device 22, along with corresponding biometric telemetry software on the individual users' computer or on a mobile computing communicating device 21. Upon successful utilization of the OEM biometric detection and collection device(s) and corresponding software, the user initializes the interface to test for connectivity and for successful communication. Upon verified communication between the user and the system, the user can log into the system.

The individual user initiates a session login on a computer or a mobile computing communicating device 21 whereby their biometric markers correlated with pertinent personal biographic information and geo-location coordinates are directed toward the COC 18 as shown in FIG. 2B. Once received by the either the CM or the AM, the information is either directed toward the DG whereby the DGM directs the individual user's data to a DB or the AM directs it to a central repository or decentralized blockchain.

Upon successful application and registration, the user logs into the system and upon successful login has full public access and use of the system. Commercial distribution is achieved by subscriber clients accessing the COC 18 as shown in FIG. 2B and requesting any number of products and or services detailed in the above embodiment. The AM is responsible for monitoring all DG's (and mirrors) for damage, data integrity, usage, scheduling regular backups and also initiates emergency backups as needed. The AM also is responsible for data backups to hard, secure off-site locations, as well as any needed restorations.

Figure 4:
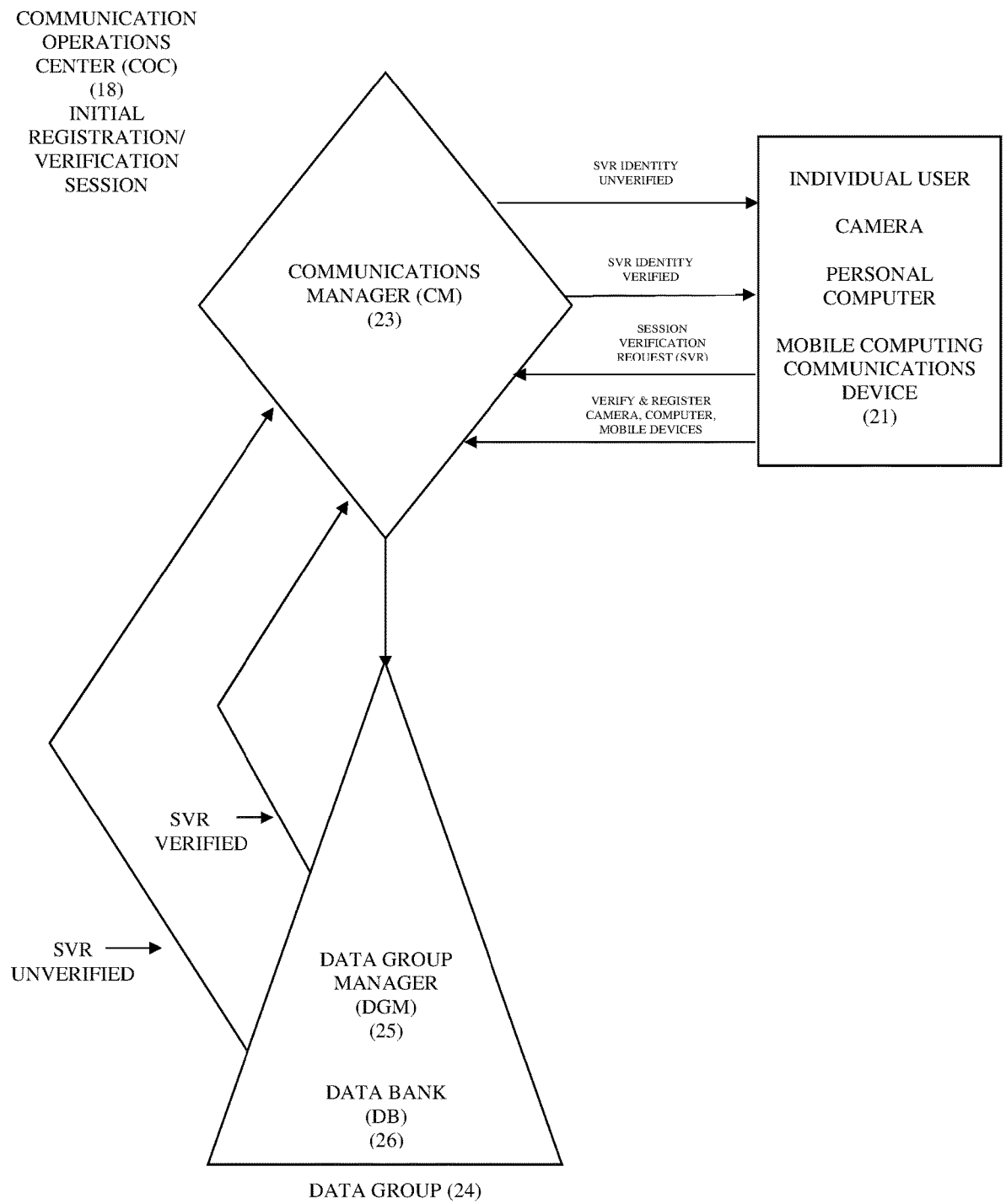
FIG. 4 is a simplified block diagram of an exemplary embodiment of the present invention of a biometric verification and individual user data management system for the initial verification of a session, illustrating the functional steps of a method of verifying biometric markers correlated with individual user data of a specific human being.

FIG. 4 is a simplified block diagram of a biometric verification and data management system for the initial identity verification of a session in an exemplary embodiment of the present invention illustrating the functional steps of a method of verifying biometric markers correlated with unique individual user data of a specific living human being.

Phase one consists of the steps for the initial session identity verification of a registered individual user. The step begins with the individual user's wired and or wireless computing communication device such as mobile phones, tablets, smart watches, gaming devices and any other Web network, or PC connected to the Internet utilizing microphones, thumbprint scanners, speakers and various style web cameras 21 as shown in FIG. 3 transmitting a session verification request (SVR) which includes biometric markers of the individual user, pertinent personal biographic information, time, geo-location coordinates and the network/IP data of the individual user's wired and or wireless computing communication devices such as mobile phones, tablets, smart watches, gaming devices and any other Web network, or PC connected to the Internet utilizing microphones, thumbprint scanners, speakers and various style web cameras 21 as shown in FIG. 3.

Upon receipt of the transmitted SVR and individual user's data, the CM 23 within the COC 18 as shown in FIG. 2B, will determine in which DG 24 the individual user's information is stored; and re-directs the SVR to the relevant DG 24. Upon receipt of the SVR and the accompanying individual user data, the DGM 25 compares the transmitted biometric markers, pertinent personal biographic information and geo-location coordinates with verified biometric markers, pertinent personal biographic information and geo-location coordinates on file at the DB 26. In addition, the DGM 25 compares the geo-location coordinates and time with the last session to determine whether the individual user could reasonably travel from the geo-location coordinates of the last session to the geo-location coordinates of the present session.

Upon the registered individual user's successful login for session use, the user's biometric markers correlated with unique pertinent personal biographic information and geo-location coordinates are directed toward the CM 23 within the COC 18 as shown in FIG. 2B. The CM 23 is responsible for receiving all SVR at user login and directing them to the DG 24 where the individual user's data is stored. Once the SVR has been processed and is either verified or rejected by the DGM 25, the CM 23 automatically returns the response to the individual user 21 waiting for verification.

Figure 7:
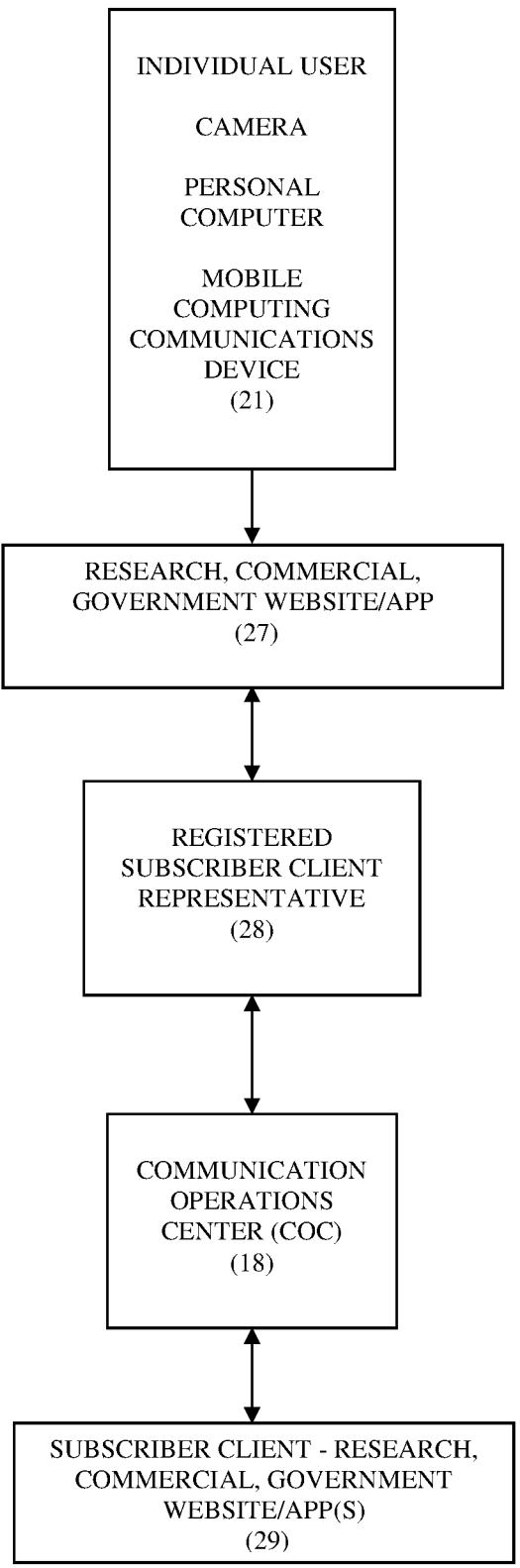
FIG. 7 is a flow chart illustrating the steps of an exemplary embodiment of a distribution method of the present invention when utilized for a particular subscriber client with the requirements of each subscriber client being unique with the present invention configured to accommodate the differing requirements of each subscriber client's distribution channels.

In the event the individual user's biometric markers, pertinent personal biographic information and geo-location coordinates match what is on file, the SVR is authenticated then said authentication is transmitted to the CM 23 of the COC 18 as shown in FIG. 2B. The CM 23 directs the SVR authentication to the registered individual user 21 and or the registered subscriber client representative 28 as shown in FIG. 7, as appropriate. Once authentication to the registered individual user 21 and or the registered subscriber client representative 28 as shown in FIG. 7 is received, they have limited system access e.g. personal profile page and live web camera feed and streaming transmission sessions.

Upon the registered individual user's 21 successful login for live web camera feed and streaming transmission session use, along with the user's biometric markers correlated with unique pertinent personal biographic information and geo-location coordinates being directed toward the CM 23 within the COC 18 as shown in FIG. 2B, the registered individual user must verify and register a camera, personal computer and or mobile computing communications device 21 as shown in FIG. 3 utilizing one or more biometric detection and collection devices 22 as shown in FIG. 3.

In the event the individual users' registered camera, personal computer and or mobile computing communications device 21 as shown in FIG. 3 utilizing one or more biometric detection and collection devices 22 is successfully verified and registered and then correlated to the individual users verified identity, the SVR is authenticated then said authentication is transmitted to the CM 23 of the COC 18 as shown in FIG. 2B. The CM 23 directs the SVR authentication to the registered individual user 21 and their registered device as approved. Once authentication of the registered individual user 21 along with their registered device 21 is received and approved, they may proceed with the live web camera feed and streaming transmission session.

The CM 23 is responsible for receiving all SVR at user login and directing them to the DG 24 where the individual user's data is stored. Once the SVR has been processed and is either verified or rejected by the DGM 25, the CM 23 automatically returns the response to the individual user 21 waiting for verification.

In the event the individual users' biometric markers, pertinent personal biographic information, geo-location coordinates, registered camera, personal computer and or mobile computing communications device utilizing one or more biometric detection and collection devices do not match what is on file, which may indicate fraud, (e.g. insufficient time for registered individual users to travel from the geo-location coordinates of the previous session to the geo-location coordinates of the present session or an unregistered device), the SVR is denied. The SVR denial is transmitted to the CM within the COC, which then transmits the rejection to the individual user and or the subscriber client. The live web camera feed and streaming transmission session is then terminated.

Figure 5:
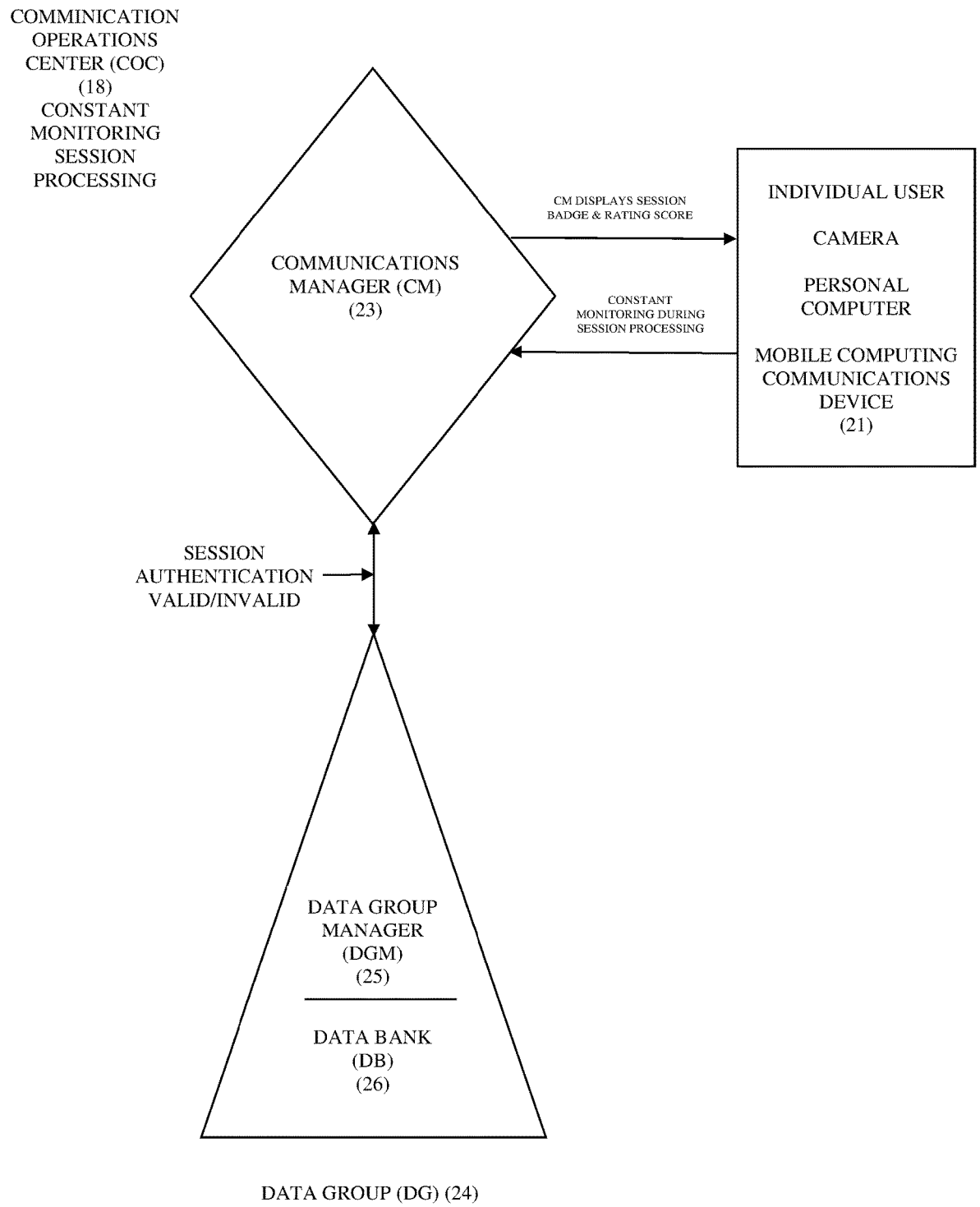
FIG. 5 is phase two of FIG. 4, a simplified block diagram of phase 2 of the exemplary embodiment of the biometric verification and individual user data management system for constantly monitoring live web camera feed and streaming transmission of video and photographic image sessions, illustrating the functional steps of monitoring within a predetermined amount of time, tracking, analyzing, storing and distributing user security badge data and dynamic, live feed biometric markers correlated with individual user data of a specific human being.

FIG. 5 is phase two of FIG. 4, a simplified block diagram of a biometric verification and data management system for a session in an exemplary embodiment of the present invention illustrating the functional steps of a method of constantly monitoring communication within a predetermined amount of time, tracking, analyzing, storing and distributing dynamic, live web camera feed and streaming transmission recording session data of a specifically identified human being.

Phase two, comprises dynamic, live web camera feed and streaming transmission constant monitoring of the session to ensure the verified registered individual user 21 is engaged in the system throughout the session. This phase comprises monitoring dynamic biometric markers to include but not limited to facial or eyelid movement, pupillary dilation or voiceprint etcetera, to maintain proof of life identification of the registered individual user during session use. The CM 23 of the COC 18 as shown in FIG. 2B directs the constant monitoring stream recording to the relevant DG 24.

The DGM 25 subjects individual users 21 to constant monitoring of biometric markers to comparisons during live web camera feed and streaming transmission use with the verified individual users' biometric markers on file. In the event monitored biometric markers continue to match and dynamic activity is maintained, the live web camera feed and streaming transmission session proceeds uninterrupted. In the event the individual users' dynamic biometric markers are absent for a predetermined period of time or if the constantly monitored biometric markers change from that of the registered individual user, a termination order is transmitted to the COC 18 as shown in FIG. 2B. The information that the individual users' dynamic biometric markers data stream is compromised, upon receipt, from the DGM 25; the COC 18 as shown in FIG. 2B times out the live web camera feed and streaming transmission session.

Figure 6:
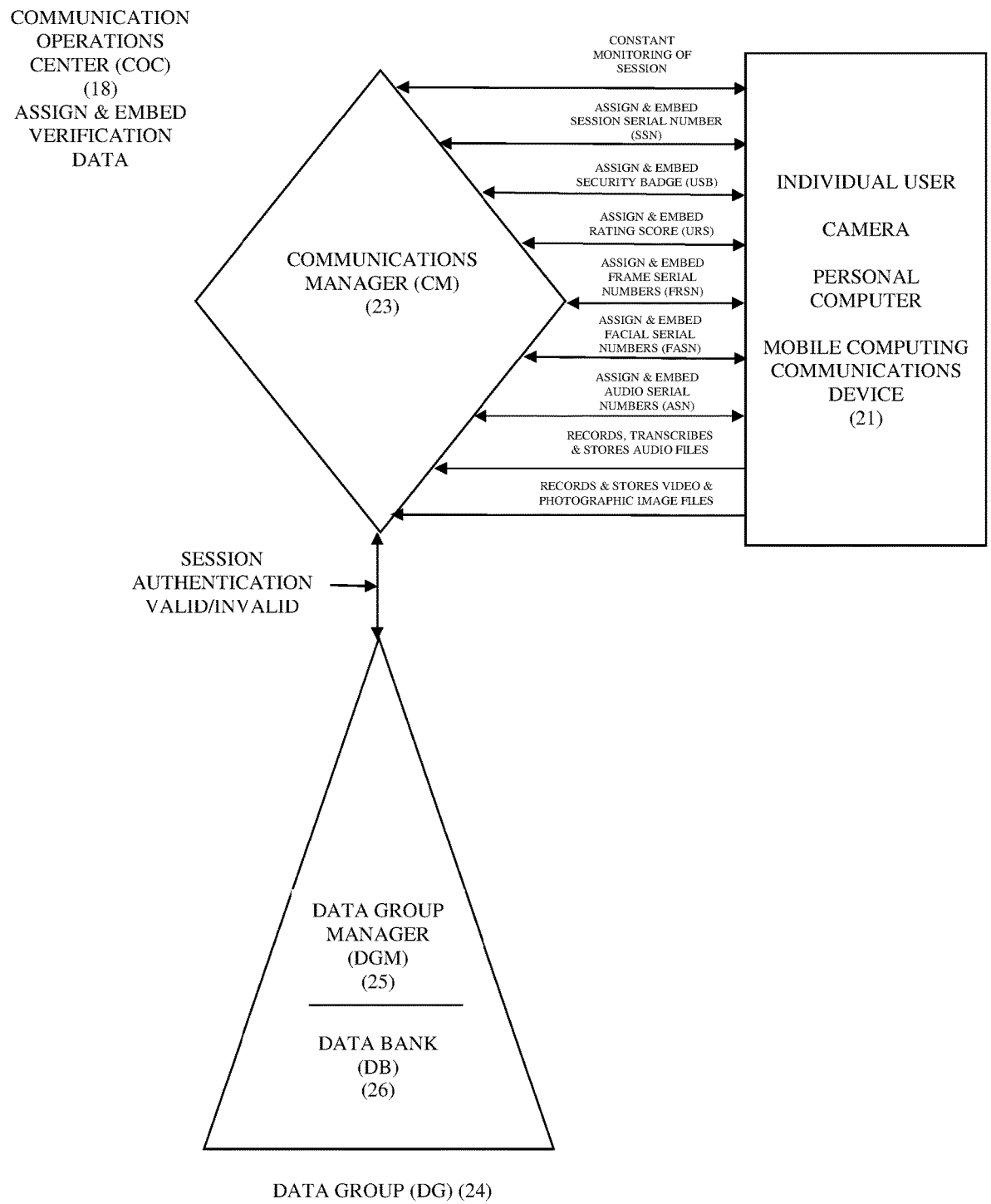
FIG. 6 is a simplified block diagram of an exemplary embodiment of phase three of FIG. 4, illustrating registered camera records a specific human being, wherein the data management system assigns and embeds indelible, detectible, hyperlinked color-coded identity verification security badge data including date/time/geo-location along with an indelible, detectable identity verification cumulative authentication rating score, encrypted, indelible, undetectable serial numbers in a predetermined audio, video and or photographic image frame, indicating an authentically recorded audio, video and or photographic image through the system.

FIG. 6 is a simplified block diagram illustrating phase three of FIG. 4, of the biometric verification and data management system for a session illustrating the functional steps of a method of constantly monitoring communication within a predetermined amount of time, tracking, analyzing, storing and distributing dynamic, live web camera feed and streaming transmission session data of a specifically identified human being as it is being recorded, followed by a method of assigning and embedding cooperative and correlative indelible, detectable and undetectable verification data such as a session serial number (SSN), a user security badge (USB), a cumulative user rating score (URS), a frame serial number (FRSN), a facial serial number (FASN), and an audio serial number (ASN) that are all interdependent of each other, while it transcribes and stores audio files, video and photographic image files within a predetermined audio, video and photographic image frame, dependent upon the registered camera recording speed, which may be directly correlated to the initial session serial number for viewing authentication.

Phase three, comprises dynamic, live web camera feed and streaming transmission constant monitoring of the session to ensure the verified registered individual user 21 is engaged in the system throughout the session. This includes monitoring dynamic biometric markers which may include, but not limited to, facial or eyelid movement, pupillary dilation or voiceprint, etcetera, to maintain proof of life identification of the registered individual user during session use. The CM 23 of the COC 18 as shown in FIG. 2B directs the constant monitoring stream to the relevant DG 24.

The DGM 25 subjects individual users 21 to constant monitoring of biometric markers to comparisons during live web camera feed and streaming transmission session use with the verified individual user's biometric markers on file. In the event monitored biometric markers continue to match and dynamic activity is maintained, the live web camera feed and streaming transmission session proceeds uninterrupted. In the event the individual user's dynamic biometric markers are absent for a predetermined period of time or, if the constantly monitored biometric markers change from that of the registered individual user, a termination order is transmitted to the COC 18 as shown in FIG. 2B. The information that the individual user's dynamic biometric markers data stream is compromised, upon receipt, from the DGM 25; the COC 18 as shown in FIG. 2B times out the live web camera feed and streaming transmission session.

During the constant monitoring process, the DGM 25 assigns and embeds through the CM 23 of the COC 18, a session serial number (SSN) that may be detectable or undetectable, into a predetermined transmitted and recorded video and or photographic image frame as the session begins. As a registered camera records a specific human being, the DGM 25 assigns and embeds through the CM 23 of the COC 18 an indelible detectable or undetectable date/time/geo-location stamp along with an encrypted indelible detectable or undetectable serial number in a predetermined video and or photographic image frame entitled a Session Serial Number, (SSN), indicating an authentically recorded video and or photographic image frame through the system.

As the live web camera feed and streaming transmission recording session continues, based on a user's successful or unsuccessful identity verification, an appropriately recognizable, standardized, indelible, detectible, hyperlinked color-coded security badge is assigned and embedded on a predetermined video and photographic image frame by the DGM 25 that is hyperlinked to the COC 18. As a registered camera records a specific human being, with identity being constantly verified, the DGM 25 assigns and embeds through the CM 23 of the COC 18 an indelible detectable, appropriately standardized, indelible, detectible, hyperlinked color-coded security badge in a predetermined frame entitled a User Security Badge (USB). In that particular frame, the verification of the specific human being indicates an authentically recorded video and or photographic image through the system.

The next stage in the live web camera feed and streaming transmission recording session consist of the DGM 25 embedding an indelible detectable, cumulative authentication rating score ranging between 0% and 100%, indicating the degree of identity verification. As a registered camera records a specific human being, with identity being constantly verified, the DGM 25 assigns and embeds, through the CM 23 of the COC 18, an indelible detectible hyperlinked identity verification cumulative authentication rating score between 0% and 100% in a predetermined frame entitled a User Rating Score (URS) that is hyperlinked to the COC 18. In that particular frame, the verification of the specific human being is displayed to indicate the degree of recorded video and or photographic image authenticity through the system.

The next stage in the live web camera feed and streaming transmission recording session consist of the DGM 25 assigning and embedding indelible detectable or undetectable serial numbers within a predetermined recorded frame. As a registered camera records a specific human being, with identity being constantly verified, the DGM 25 assigns and embeds through the CM 23 of the COC 18 an indelible detectable or undetectable date/time/geo-location stamp along with an encrypted indelible detectable or undetectable serial number, in a predetermined frame, entitled a Frame Serial Number (FRSN), within each predetermined frame, indicating the authentication of that particular frame and an authentically recorded video and or photographic image through the system.

The next stage in the live web camera feed and streaming transmission recording session consist of the DGM 25 assigning and embedding indelible detectable or undetectable serial numbers within the users face within a predetermined recorded frame. As a registered camera records a specific human being, with identity being constantly verified, the DGM 25 assigns and embeds, through the CM 23 of the COC 18, an indelible detectable or undetectable date/time/geo-location stamp along with an encrypted indelible undetectable serial number, in a predetermined frame, entitled a Facial Serial Number (FASN), within each specific human beings face, in that particular frame, the authentication of the specific human being, indicating an authentically recorded video and or photographic image through the system.

The next stage in the live web camera feed and streaming transmission recording session consist of the DGM 25 assigning and embedding indelible detectable or undetectable serial numbers within an audio file within a predetermined frame. As a registered camera records a specific human being, the DGM 25 assigns and embeds, through the CM 23 of the COC 18, an indelible detectable or undetectable date/time/geo-location stamp along with an encrypted indelible undetectable serial number in a predetermined audio frame file entitled an Audio Serial Number (ASN), indicating authentically recorded audio through the system.

The next stage in the live web camera feed and streaming transmission recording session consist of the DGM 25 recording, transcribing and storing all recorded audio files indelibly in the systems distributed DB's along with an encrypted indelible serial number entitled an Audio Serial Number (ASN) from predetermined audio frame files of a specific human being, enabling the verification and auditing of recorded audio files through the system for authenticity.

The final stage in the live web camera feed and streaming transmission recording session consist of the DGM 25 recording and storing all transmitted video and photographic image files indelibly in the systems distributed DB's along with an encrypted indelible User Security Badge (USB), User Rating Score (URS), Frame Serial Number (FRSN) and Facial Serial Number (FASN) from predetermined video and photographic image frame files, enabling the verification and auditing of recorded video and photographic image files through the system for authenticity.

FIG. 7 is a flow chart illustrating the steps of an exemplary embodiment of a method of commercial distribution of the present invention when utilized for a commercial and or government subscriber client. This embodiment of the present invention is designed to accommodate the differing distribution channel requirements of commercial and or government subscriber clients. The process begins with the individual user 21 logging in to an individual user's commercial and or government website 27 of choice. Upon login, the selected commercial and or government website 27 directs the individual user's wired and or wireless computing communication devices such as, for example, mobile phones, tablets, smart watches, gaming devices and any other Web network, or PC connected to the Internet utilizing microphones, thumbprint scanners, speakers and various style web cameras 21 to access the individual user's dynamic biometric markers and or live web camera feed and streaming transmission session and or recorded data, directed toward the systems COC 18 as shown in FIG. 2B.

Upon receipt of the individual user's dynamic biometric markers and or live web camera feed and streaming transmission session data, the COC 18 as shown in FIG. 2B verifies or rejects the individual user's identity. Upon verification, the registered subscriber client representatives' individual biometric markers 28 within the COC 18 acts as a portal to the subscriber clients commercial and or government website(s) 29. Throughout the system's live web camera feed and streaming transmission session and or recording use, the COC 18 constantly monitors the individual users' dynamic biometric markers and or live web camera feed and streaming transmission session and or recording data. Should the registered individual user's dynamic biometric markers and or live web camera feed and streaming transmission session and or recording data become compromised, the COC 18 terminates the live web camera feed and streaming transmission and or recording session and informs the commercial and or government subscriber client and their representative of a possible security breach.

Figure 8:
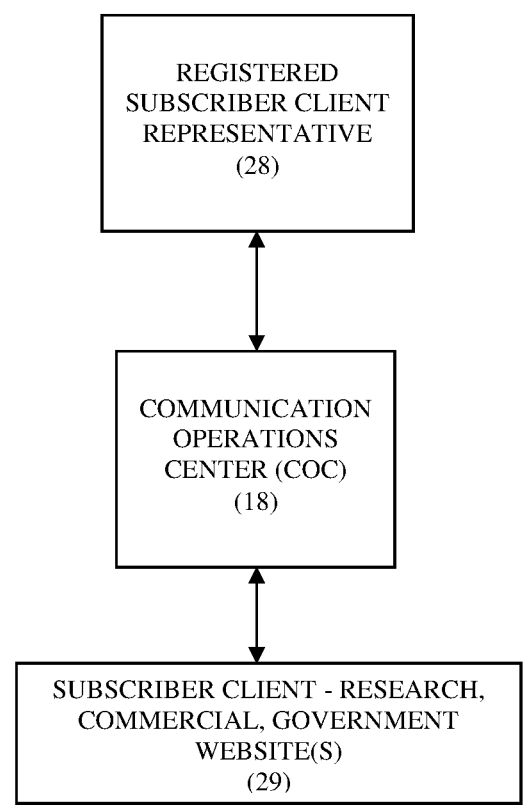
FIG. 8 is a flow chart illustrating the steps of an exemplary embodiment of an alternate distribution method of the present invention when utilized for a particular subscriber client with the requirements of each subscriber client being unique with the present invention configured to accommodate the differing requirements of the subscriber client's distribution channels.

FIG. 8 is a flow chart illustrating the steps of an exemplary embodiment of an alternate method of distribution of the present invention when utilized for a particular commercial and or government subscriber client with the requirements of each commercial and or government subscriber client being unique. This embodiment of the present invention is designed to accommodate the differing requirements of a commercial and or government subscriber client's distribution channels. The registered individual user 21 logs into the systems COC 18 as shown in FIG. 2B where upon the individual user 21 is either verified or rejected. Upon the verification, the registered subscriber client representatives' biometric markers 28, within the systems COC 18 which acts as a portal to the verified individual users 21 commercial and or government website(s) 29 of choice. Throughout the live web camera feed and streaming transmission and or recording session use, the system COC 18 constantly monitors the registered individual user's 21 dynamic biometric markers and or live web camera feed and streaming transmission session and or recording data. If no discrepancies arise, the live web camera feed and streaming transmission and or recording session continues unabated. Should the individual user's 21 dynamic biometric markers and or live web camera feed and streaming transmission and or recording data become compromised, the live web camera feed and streaming transmission and or recording session is terminated and the individual user 21 is notified of the possible security breach.

FIG. 9 is a sequence diagram that depicts a sequence of steps between a user and the Communication Operations Center (COC) that are performed by different elements in FIG. 1 through FIG. 8, according to an embodiment of the invention as it provides a uniform communication bidirectional layer for the systems live web camera feed and streaming transmission session.

Operations Performed by a User

In step U1, user 21 begins the process by applying and registering for membership of the live web camera feed and streaming transmission system. Once the application and registration process has been successfully completed, the user completes login to the systems website or app.

In step U2, the user 21 begins the user identity verification process as shown in the systems COC 18 (FIG. 4). Once completed, user verifies and registers the user's device and geo-location according as described previously.

In step U3, the user 21 enters their personal profile page to ensure personal biographic information is current. The user titles the pending live web camera feed and streaming transmission session to participate in the system. The user selects a public identity that may include their legal identity or an alias and or personalized avatar to maintain anonymity in the public forum. Finally, the user searches for available live web camera feed and streaming transmission session times.

In step U4, the user 21 verifies then schedules a live web camera feed and streaming transmission session once a real-time live stream push notification via an SMS message, email, or other message via another "external" notification channel from the user via the Cloud Server 150 is received by the Communication Operations Center 18, as shown in FIG. 4, demonstrating a request to initiate a live web camera feed and streaming transmission session and acknowledged. For example, a response to an SMS message might include the following text, "You are invited to initiate your live stream at the proposed time and date".

In step U5, the user 21 initiates the live web camera feed and streaming transmission session after the proposed scheduled live web camera feed and streaming transmission invitation is confirmed and authorized by the Communication Operations Center 18. In the event that a Communication Operations Center rejects the request from a user, the user is notified and can restart the search process for an available date/time slot for a live web camera feed and streaming transmission session. Upon confirming the live web camera feed and streaming transmission session from the Communication Operations Center 18, and during the live web camera feed and streaming transmission session, the user 21 will be constantly monitored to determine identity verification. An appropriately recognizable and standardized, indelible, detectable, hyperlinked color-coded security badge will be embedded and displayed on a predetermined video frame or photographic image based on their successful or unsuccessful identity verification to be embedded by the Communication Operations Center 18. Additionally, the Communication Operations Center 18 will embed and display an indelible hyperlinked cumulative authentication rating score between 0% to 100% based on their successful or unsuccessful identity verification on a predetermined video frame or photographic image. Based on the user's 21 unsuccessful identity verification, the Communication Operations Center 18 can choose to discontinue the users 21 access to the current live web camera feed and streaming transmission session. Based on the users 21 successful identity verification, the Communication Operations Center 18 can continue with authorized access to the current live web camera feed and streaming transmission session.

In step U6, the user 21 may initiate or accept to end the live web camera feed and streaming transmission session with the Communication Operations Center 18. Once this task is completed, the user 21 may choose to edit the live web camera feed and streaming transmission session recording. Once this task is completed, the user 21 may choose to provide feedback and or rate the experience for the completed live web camera feed and streaming transmission session. At this stage, the user 21 may receive notification by the system of invention of a contribution being added to their frequent reward program in the form of commercial discounts, credits and or points, which is located in the users 21 personal profile page. The user's 21 live web camera feed and streaming transmission session recording data, biometric marker data and or personal biographic information may now be prepared for commercial distribution and or posted on subscriber client's 29 websites. Finally, all live web camera feed and streaming transmission session recording data may be stored for future commercial reference, disinterested third party authentication and or professional auditing.

Operations Performed by the Communication Operation Center

In step C1, the Communication Operations Center 18 begins the process by evaluating the membership application and registration submission for the live web camera feed and streaming transmission system. Once the application and registration process has been successfully completed, the Communication Operations Center 18 acknowledges login to the systems website or app.

In step C2, the Communication Operations Center 18 evaluates the user's 21 personal profile page to ensure personal biographic information is current. The Communication Operations Center 18 begins the user 21 identity verification process in the system's COC 18 as shown in FIG. 4. Once completed, the Communication Operations Center verifies the user's device and geo-location.

In step C3, the Communication Operations Center 18 acknowledges a request by the user 21 to schedule a live web camera feed and streaming transmission session via an SMS message, email, or other message via another "external" notification channel, requesting to initiate a live web camera feed and streaming transmission session via the Cloud Server 150 received by the COC (18) 160 as shown in FIG. 1. For example, a response to an SMS message might include the following text, "You are invited to initiate your live stream at the proposed time and date". The Communication Operations Center 18 acknowledges a public identity that may include the users 21 legal identity or an alias and or an avatar to maintain anonymity in the public forum. The Communication Operations Center 18 then evaluates and records the live web camera feed and streaming transmission session recording title. Finally, the Communication Operations Center 18 assigns an indelible Session Serial Number (SSN) to be embedded into a predetermined video and or photographic image frame.

In step C4, the Communication Operations Center 18 schedules and initiates a live web camera feed and streaming transmission session by notifying the user 21 via an SMS message, email, or other message via another "external" notification channel from the user via the Cloud Server 150, agreeing to a request to initiate a live web camera feed and streaming transmission session. For example, a response to an SMS message might include the following text, "Your live stream at the proposed time and date is confirmed". The Communication Operations Center 18 then verifies the identity of the user 21 once the live web camera feed and streaming transmission session recording begins. The Communication Operations Center 18 then assigns, embeds and displays an appropriately recognizable and standardized, indelible, detectible, hyperlinked color-coded security badge entitled User Security Badge (USB) based on the users successful or unsuccessful identity verification to be recorded on to a predetermined frame of the live web camera feed and streaming transmission session. Finally, the Communication Operations Center 18 embeds and displays on a predetermined video and or photographic image frame, an indelible detectible hyperlinked identity verification cumulative authentication rating score between 0% and 100% to be viewed through subscriber client's media platforms. Based on the user's 21 successful identity verification, the user can continue with authorized access to the current live web camera feed and streaming transmission session.

In step C5, the Communication Operations Center 18 initiated the live web camera feed and streaming transmission upload after the proposed scheduled live web camera feed and streaming transmission connection is verified then initiated by the user 21 and confirmed by the Communication Operations Center 18. In the event that a Communication Operations Center 18 rejects the live web camera feed and streaming transmission from the user, the user is notified. Upon initiating the live web camera feed and streaming transmission session and during the live web camera feed and streaming transmission session, the Communication Operations Center 18 constantly monitors the user to determine identity verification. Based on the user's successful identity verification, the Communication Operations Center 18 assigns and embeds an indelible, detectable or undetectable serial number entitled a Frame Serial Number (FRSN) on a predetermined video and or photographic image frame. Based on the user's successful identity verification, the Communication Operations Center 18 assigns and embeds an indelible, detectable or undetectable serial number entitled a Facial Serial Number (FASN) on the recorded users face on a predetermined video and or photographic image frame. Based on the user's successful identity verification, the Communication Operations Center assigns and embeds an indelible, detectable or undetectable serial number entitled an Audio Serial Number (ASN) on a predetermined audio file frame. Based on the user's unsuccessful identity verification, the Communication Operations Center 18 can choose to discontinue the user's access to the current live web camera feed and streaming transmission session. Based on the user's successful identity verification, the Communication Operations Center 18 can choose to continue the users authorized access to the current live web camera feed and streaming transmission session.

In step C6, the user 21 may initiate or accept to end the live web camera feed and streaming transmission session with the Communication Operations Center 18. Based on the experience for the completed session recording, the user 21 may submit feedback that can be registered by the Communication Operations Center 18 and contained within the user's 21 personal profile page. At this stage, the user 21 may receive notification by the Communication Operations Center 18 of a contribution being added to their frequent user 21 reward program in the form of commercial discounts, credits and or points, which is located in the users 21 personal profile page. The Communication Operations Center 18 transcribes the recorded audio data and makes it available to subscriber clients through the embedded and displayed, appropriately recognizable and standardized, indelible, detectible, hyperlinked color-coded security badge entitled User Security Badge (USB) which may include the users 21 biometric marker data and personal biographic information which is stored and may now be prepared for commercial distribution. Finally, all live web camera feed and streaming transmission recording data may be stored for future subscriber clients, commercial reference, disinterested third party authentication and or professional auditing.

While the present invention has been disclosed in various preferred forms, the specific embodiments thereof as disclosed and illustrated herein are considered as illustrative only of the principles of the invention and are not to be considered in a limiting sense in interpreting the claims. The claims are intended to include all novel and non-obvious combinations and sub-combinations of the various elements, features, functions, and/or properties disclosed herein. Variations in size, materials, shape, form, function and manner of operation, assembly and use, are deemed readily apparent and obvious to one skilled in the art from this disclosure, and all equivalent relationships to those illustrated in the drawings and described in the specification are intended to be encompassed in the following claims defining the present invention.

The invention claimed is:

1. A secure live web camera feed and streaming transmission method with definitive online identity verification for collecting dynamic biometric information and prevention of synthetic video and photographic images of a specific human being for personal, commercial and government markets when enrolled in a secure live web camera feed and streaming transmission system, the method comprising the steps of:

utilizing a registered biometric detection and collection device by the individual user in order to apply and register for access to the live web camera feed and streaming transmission system and associated with at least one or more live video and photographic images;

gathering, identifying, authenticating and registering individual user biometric markers prompted by a mechanism to incentivize the individual user with greater security, public anonymity and a reward program, by utilizing a registered biometric detection and collection device by the individual user; biometric markers including at least one or more of facial patterns, facial or eyelid movement, pupillary dilation and voiceprint; and interfacing with a government agency to verify proof of life identification through a wired or wireless computing communication device such as mobile phones, tablets, smart watches and any other Web network, or PC connected to the Internet utilizing microphones, thumbprint scanners, speakers and various style web cameras, a sufficient amount of said biometric markers correlated with uniquely pertinent personal biographic information collected directly from an individual user to authenticate the identity of the individual user gathered by the registered biometric detection and collection device interfacing through a registered wired or wireless computing communication device such as mobile phones, tablets, smart watches and any other Web network, or PC connected to the Internet utilizing microphones, thumbprint scanners, speakers and various style web cameras; and upon denial of authentication, notifying the applicant user of the rejection and that the applicant user may reapply for access to the live web camera feed and streaming transmission system, and upon verification of authentication, notifying the applicant user of the verification and the applicant user may register for access to the live web camera feed and streaming transmission system via electronic means and become a registered user;

constantly monitoring, tracking and analyzing the live web camera feed and streaming transmission for dynamically gathered biometric information of the registered user correlated with uniquely pertinent personal biographic information, geo-location coordinates and live web camera feed and streaming transmission recorded session data stored at a selected data bank in a biometric verification and data management system having a plurality of data banks at multiple levels of a database or decentralized blockchain, wherein said constant live stream dynamic monitoring, tracking and analyzing steps include selecting the data bank based on the uniquely pertinent personal biographic information and geo-location coordinates gathered from the individual user to commercially utilize the live web camera feed and streaming transmission dynamic individual user data associated via electronic means with the at least one or more live video and photographic images and at least one or more of facial patterns, facial or eyelid movement, pupillary dilation and voiceprint biomarkers; and receiving with the data management system—inclusive of a data group manager serving as a database controller and processing center session—verification requests from a communication manager processor; and embedding in the recorded session data cooperative and correlative indelible, encrypted, biometric information to include at least one or more of a facial serial number, a voice print (audio file) serial numbers, and video frame serial numbers within predetermined video and photographic image frames.

2. The method according to claim 1, wherein said biometric markers and uniquely pertinent personal biographic information selected from a group consisting of individual user biometric markers also include gathering one or more or a plurality of such, as an electronic facial image, voice print, or thumbprint, and may include but not limited to the individual users' name, alias, birth date, city/state and/or country of birth, physical description and characteristics, parents married and maiden name(s), current residential and employment address(es), current and past employer(s), preferred password, social security number, specific interests, academic achievement and other similar information, in order to apply for access to the system.

3. The method according to claim 2, wherein said step of gathering individual user biometric markers also include:

gathering the individual user's categorical selection of personal interests to develop a unique profile for the applying individual user in the business to business (B2B), business to consumer (B2C) and consumer to consumer (C2C) within personal, commercial and government market models.

4. The method according to claim 2, wherein said individual user biometric markers also include an electronic image of a government issued form of identification selected from the group consisting of a driver's license, military, state or national identification card or passport, to be compared with the individual user's identification on file and on record with the issuing government agency via electronic means in order to apply for access to the live web camera feed and streaming transmission system and provide quality control authentication; and when verified, notifying the individual user then providing a method for the verified individual user to register for a commercial coupon, consumer discount, and or frequent user loyalty/reward program in various markets.

5. The method according to claim 4, comprising the further the step of:

allowing the individual registered user to select the manner in which their government authenticated identity is to be publicly reflected by selecting public disclosure identification options from the group consisting of the individual registered user's government authenticated identification, an alias, and or an avatar for selected apps and or websites including commercial websites, government websites, and social networks to maintain security to the live web camera feed and streaming transmission system.

6. The method according to claim 1, wherein said step of constantly monitoring individual user biometric markers comprises:

monitoring constant live stream dynamic human interaction while logged on to the identity verification system for proof of life identification selected from the group consisting of facial or eyelid movement, pupillary or retinal dilation, voice print and or finger print placement collected by said biometric detection and collection device.

7. The method according to claim 6, comprising the further step of:

constantly monitoring the registered user's collected biometric markers and system usage in order to ensure that continued access to the secured live web camera feed and streaming transmission system remains authorized, and to time-out upon the absence of any of the biometric markers of the registered user when absent for a predetermined amount of time and block the registered user from continuous uninterrupted authorized access to either of registered computer systems or programs in the identity verification system.

8. The method according to claim 1, comprising the further step of:

storing the monitored, tracked, and analyzed unique and comprehensive profile of the registered user and live web camera feed and streaming transmission session data with the assignment of a uniform resource locator (URL) to be posted on video service platforms and providing editing tools for storage capability in a central repository and or decentralized blockchain and the live posting without editing, making it available to registered commercial and or government entities via electronic means.

9. The method according to claim 8, wherein said step of making said stored unique and comprehensive profile of the registered user and live web camera feed and streaming transmission session data warehoused in a central repository and or decentralized blockchain available to commercial and or government entities, comprises:

requiring the registration and verification of the commercial and or government entity representative with the present identity verification system, and once registered and verified, allowing the commercial and or government entity representative access to the dynamically collected data of the registered user including a unique and comprehensive profile of the registered user as one or a plurality of transactions including unique individual biometric markers or a comprehensive profile complete with cataloged, collated and analytical projections of a potential sequential course of the individual user to take in all individually unique physical and audio mannerisms within the system of invention; and utilizing the registered and verified biometric detection and collection device selected from the group consisting of:

registered computer ready camera, a microphone, a bio-metric mouse and or touch pad for authenticating dynamic registered user identification to aid commercial and or government websites and banking institutions in identity theft prevention endeavors, authenticating dynamic registered user identification to aid consumer security-background check companies in anti-identity theft endeavors; a registered computer ready camera, a microphone, a bio-metric mouse and or touch pad and an infrared scanner for authenticating dynamic registered user identification to aid employers in workplace enforcement for employees on-site, traveling, teleconferencing or telecommuting, and authenticating dynamic registered user identification to aid academic institutions in conducting rollcall or proctoring online testing; a registered computer ready camera, microphone, computer ready camera, a microphone, a bio-metric mouse and or touch pad for authenticating dynamic registered user identification to aid in accessing or preventing access to building structures, to aid in accessing or preventing access to air transportation, to aid in accessing or preventing access to boat craft;

a computer ready camera, a microphone, a bio-metric mouse and or touch pad for authenticating dynamic registered user identification to aid rating, polling, authentic marketing and research campaigns; a registered computer ready camera, a microphone, a bio-metric mouse and or touch pad for authenticating dynamic registered user identification to aid in regulatory/law enforcement, government programs, intelligence utilization and fraud detection;

a computer ready camera, a microphone, a bio-metric mouse and or touch pad for authenticating dynamic registered user identification to aid in creating a biometric collage of current users to reflect and display a constantly evolving face, in mind reading video production and the detection of a specific human being versus a robot or artificial intelligence humanoid of a specific human being in video and photographic image production; a computer ready camera, a microphone, a bio-metric mouse and or touch pad for authenticating dynamic registered user identification to aid users and their legal representatives in reverse image search engines and for reverse voice recognition search engines for facial and voice recognition cease and desist endeavors;

a registered computer ready camera, microphone, computer ready camera, a microphone, a bio-metric mouse and or touch pad for authenticating dynamic registered user identification to aid users and their legal representatives in licensing protected live web camera feed and streaming transmission media, enforcing residual and royalty agreements, synthetic video and photographic image detection by providing notarized and certified data sets for comparative models and notary publics to authenticate the execution of documents;

a registered computer ready camera, a microphone, a bio-metric mouse and or touch pad;

providing compensation, monetary credit, a donation credit or an incentive to an online banking repository or commercial institution, a donation credit or incentive to a non-profit organization, or an amount or value incentive of a frequent user reward program for the registered user to redeem; and providing at least one of a corresponding electronic/digital graphs, charts, logs, tables, records or meters to plot the identity verification system's use for registered users and registered commercial and or government entities for business to business (B2B), business to consumer (B2C) and consumer to consumer (C2C) commercial markets within the live web camera feed and streaming transmission system.

10. A computer implemented live web camera feed and streaming transmission system for harvesting dynamic biometric information of an individual user for personal, commercial and or government distribution and prevention of synthetic video and photographic images, the system comprising:

server coupled with a computer processor having memory storage and computer executable software programs stored therein;

a biometric detection and collection device connected in communication with said processor and operative upon instructions from said computer program instructions to gather dynamic biometric information and live web camera feed and streaming transmission session data from the individual user and associated with at least one or more live video and photographic images;

a registered biometric detection and collection device interfaced in communication with wired or wireless computing communication devices such as mobile phones, tablets, smart watches and any other Web network, or PC connected to the Internet utilizing microphones, thumbprint scanners, speakers and various style web cameras and interfaced in communication with a government agency;

upon execution of software program instructions by said computer processor, said biometric detection and collection device and said wired or wireless computing communication device such as mobile phones, tablets, smart watches and any other Web network, or PC connected to the Internet utilizing microphones, thumbprint scanners, speakers and various style web cameras are caused to gather biometric markers and uniquely personal biographic information directly from an individual user to authenticate the identity and proof of life identification of the individual user, and the geo-location to identify the latitude and longitude to specifically locate the individual user;

a communication operations center configured to receive session verification requests of the gathered biometric markers, uniquely personal biographic information, and geo-location coordinates and direct them to a selected data group in a biometric verification and data management system having a plurality of data banks at multiple levels of a database, and having a data group manager program configured to select the database and or decentralized blockchain based on the uniquely personal biographic information and geo-location coordinates gathered from the individual user;

said biometric markers including at least one or more of facial patterns, facial or eyelid movement, pupillary dilation and voiceprint;

said biometric detection and collection device configured to gather through said interfacing registered wired or wireless computing communication device such as mobile phones, tablets, smart watches and any other Web network, or PC connected to the Internet utilizing microphones, thumbprint scanners, speakers and various style web cameras, biometric markers, uniquely personal biographic information, geo-location coordinates, and unique identifiers directly from an individual user, selected from a group consisting of their name, alias, birth date, city/state and/or country of birth, physical description and characteristics, parents married and maiden name(s), current address(es), current and past employer(s), preferred password, social security number, specific interests, and other similar information, categorical selection of interests and related information;

said biometric detection and collection device interfaced with a registered wired or wireless computing communication device such as mobile phones, tablets, smart watches and any other Web network, or PC connected to the Internet utilizing microphones, thumbprint scanners, speakers and various style web cameras that transmits the gathered biometric markers, uniquely pertinent personal biographic information and geo-location coordinates over a wired or wired or wireless connection to a central repository and or decentralized blockchain for facilitation of identification verification;

said central repository and or decentralized blockchain facilitates identification verification in conjunction with a communication manager processor and an archive manager processor within a communication operations center, said communication manager processor is configured to receive at login, a session verification request of the gathered biometric markers, uniquely pertinent personal biographic information, and geo-location coordinates to direct the biometric markers, uniquely pertinent personal biographic information, geo-location coordinates and live web camera feed and streaming transmission recorded session data to a selected data group where the individual user data is stored to be processed and either verified or rejected by the data group manager which automatically returns the response to the individual user waiting for verification in the form of an appropriate and standardized, indelible, detectible, hyperlinked color-coded security badge to verify media data authenticity (transcribed audio files, date/time/geo-location, identity verification, etc.) through the system servers and an indelible, detectable identity verification cumulative authentication rating score between 0%-100%; said archive manager processor monitors all the data group data for damage, data integrity, usage, scheduling of regular backups, initiates emergency backups as needed and is responsible for data backups to hard, secure off-site locations, as well as any needed restorations;

said communication manager processor configured to randomly store the gathered biometric markers, uniquely pertinent personal biographic information and geo-location coordinates separately to the selected data group manager processor then randomly send a separate copy of the biometric markers, uniquely pertinent personal biographic information and geo-location coordinates to the selected database which are location independent and or decentralized blockchain when all system components are networked using an ultra-high-speed network;

said data group manager serving as the database controller and processing center that receives a session verification request from the communication manager processor, then accesses the database where the individual user's biometric data is stored and evaluates the session verification request to determine if the individual user matches the gathered biometric data, the data group manager monitors the time used for each individual user session verification request and if, due to traffic density, this response time exceeds a maximum response time threshold, will automatically route session verification requests to as many mirror sites as necessary to remain within the required response time; said database is a computer server that stores the individual user's biometric data and evaluates the session verification request to determine if the individual user matches the individual user that the biometric data belongs to where a session verification request is received from the communication manager, the data group manager will access the database and or decentralized blockchain;

data group mirror sites are used to maintain processing speed and response time during periods of high demand;

said archive manager processor monitors all the data group data for damage, data integrity, usage, scheduling of regular backups, initiates emergency backups as needed and is responsible for data backups to hard, secure off-site locations, as well as any needed restorations; and said communication manager processor is configured to embed cooperative and correlative indelible, encrypted, undetectable session serial numbers, facial serial numbers, voice print (audio file) serial numbers and video frame serial numbers within predetermined video and photographic image frames then randomly store the live web camera feed and streaming transmission data.

11. The system according to claim 10, wherein said biometric detection and collection device is configured to gather biometric information from the individual user through said interfaced registered wired or wireless computing communication device such as mobile phones, tablets, smart watches and any other Web network, or PC connected to the Internet utilizing microphones, thumbprint scanners, speakers and various style web cameras and is electronically interfaced in communication with a government agency to authenticate identification with biometric markers and uniquely pertinent personal biographic information of said individual user through said system server.

12. The system according to claim 10, wherein said communication operations center includes a communication manager processor configured to analyze the biometric markers, uniquely pertinent personal biographic information, and geo-location coordinates to identify patterns for developing a unique profile; and a data group processor interfaced with said communication manager processor configured to select a database and or decentralized blockchain corresponding to said identified patterns.

13. The system according to claim 12, wherein said communication manager processor is further configured to analyze the biometric markers, uniquely pertinent personal biographic information, and geo-location coordinates to authenticate the individual user's proof of life identification with a government agency, and to select a database and or decentralized blockchain based on the identified patterns of biometric markers correlated with uniquely pertinent personal biographic information and geo-location coordinates.

14. The system according to claim 13, wherein said communication manager processor is further configured to select a local database at a local level of the database and or decentralized blockchain when the biometric markers, uniquely pertinent personal biographic information, and geo-location coordinates gathered from the individual user indicates that the individual user may be located in an associated local area for more than a threshold period of time and for less than the threshold period of time.

15. The system according to claim 10, wherein said biometric detection and collection device includes at least one of a registered camera, a microphone, a biometric computer mouse, a touch pad, a thermometer, a pulse detector and a respiration detector.

16. The system according to claim 10, further comprising; a registered wired or wireless computing communication device such as mobile phones, tablets, smart watches and any other Web network, or PC connected to the Internet utilizing microphones, thumbprint scanners, speakers and various style web cameras configured to receive through an input mechanism, the unique identification number of an unverified individual user; gather through a biometric detection and collection device, new biometric markers, uniquely pertinent personal biographic information and geo-location coordinates from the unverified individual user; and transmit the unique identification number and new biometric markers, uniquely pertinent personal biographic information and geo-location coordinates, interfacing with a registered wired or wireless computing communication device such as mobile phones, tablets, smart watches and any other Web network, or PC connected to the Internet utilizing microphones, thumbprint scanners, speakers and various style web cameras over a wired or wired or wireless connection to a communication manager processor with a session verification request to authenticate the identity of the unverified individual user with a government agency; and to receive a positive or negative verification response from the government agency to authenticate proof of life identification or reject authenticity of the proof of life identification.

17. The system according to claim 16, wherein said authentication of the identity of an unverified individual user with a government agency to verify proof of life identification is to be conducted by the individual users to decode with, by, but not limited to a PDF417 two-dimensional high-density stacked linear barcode, capable of encoding text, files and data bytes, or similar, such as Optical Character Recognition, Ultra Violet Lighting and Hologram detection that may contain biometric data and pertinent personal biographic information that is often included on a current government issued driver's license, military, state or national ID or passport, communicating via computer interface with the corresponding state or federal government agency that is responsible for authentication of government issued forms of identification.

18. A computer implemented live web camera feed and streaming transmission system for harvesting dynamic biometric information of an individual user for personal, commercial and or government distribution and prevention of synthetic video and photographic images, the system comprising:
- a server coupled with a computer processor having memory storage and computer executable software programs stored therein;
- a biometric detection and collection device connected in communication with said processor and operative upon instructions from said computer program instructions to gather dynamic biometric information and live web camera feed and streaming transmission session data from the individual user and associated with at least one or more live video and photographic images;
- a registered biometric detection and collection device interfaced in communication with wired or wireless computing communication devices such as mobile phones, tablets, smart watches and any other Web network, or PC connected to the Internet utilizing microphones, thumbprint scanners, speakers and various style web cameras and interfaced in communication with a government agency;
- upon execution of software program instructions by said computer processor, said biometric detection and collection device and said wired or wireless computing communication device such as mobile phones, tablets, smart watches and any other Web network, or PC connected to the Internet utilizing microphones, thumbprint scanners, speakers and various style web cameras are caused to gather biometric markers and uniquely personal biographic information directly from an individual user to authenticate the identity and proof of life identification of the individual user, and the geo-location to identify the latitude and longitude to specifically locate the individual user; and
- a communication operations center configured to receive session verification requests of the gathered biometric markers, uniquely personal biographic information, and geo-location coordinates and direct them to a selected data group in a biometric verification and data management system having a plurality of data banks at multiple levels of a database, and having a data group manager program configured to select the database and or decentralized blockchain based on the uniquely personal biographic information and geo-location coordinates gathered from the individual user;
- said biometric detection and collection device configured to gather through said interfacing registered wired or wireless computing communication device unique identifiers directly from an individual user;
- said biometric detection and collection device interfaced with a registered wired or wireless computing communication device such as mobile phones, tablets, smart watches and any other Web network, or PC connected to the Internet utilizing microphones, thumbprint scanners, speakers and various style web cameras that transmits the gathered biometric markers, uniquely pertinent personal biographic information and geo-location coordinates over a wired or wired or wireless connection to a central repository and or decentralized blockchain for facilitation of identification verification;
- said central repository and or decentralized blockchain facilitates identification verification in conjunction with a communication manager processor and an archive manager processor within a communication operations center, said communication manager processor is configured to receive at login, a session verification request of the gathered biometric markers, uniquely pertinent personal biographic information, and geo-location coordinates to direct the biometric markers, uniquely pertinent personal biographic information, geo-location coordinates and live web camera feed and streaming transmission recorded session data to a selected data group where the individual user data is stored to be processed and either verified or rejected by the data group manager which automatically returns the response to the individual user, the individual user data stored to be processed and verified or rejected by the data group manager, which automatically returns the response to the individual user waiting for identity verification through the system servers and an indelible, detectable identity verification cumulative authentication rating score between 0%-100%;

said data group manager serves as the database controller and processing center that receives a session verification request from the communication manager processor, then accesses the database where the individual user's biometric data is stored and evaluates the session verification request to determine if the individual user matches the gathered biometric data, the data group manager monitors the time used for each individual user session verification request and if, due to traffic density, this response time exceeds a maximum response time threshold, will automatically route session verification requests to as many mirror sites as necessary to remain within the required response time;

said database is a computer server that stores the individual user's biometric data and evaluates the session verification request to determine if the individual user matches the individual user that the biometric data belongs to where a session verification request is received from the communication manager, the data group manager will access the database and or decentralized blockchain; and data group mirror sites are used to maintain processing speed and response time said archive manager processor monitors the data group data for damage, data integrity, usage, scheduling of regular backups, initiates emergency backups as needed and is responsible for data backups to hard, secure off-site locations, as well as any needed restorations; and said communication manager processor is configured to embed cooperative and correlative indelible, encrypted, undetectable session serial numbers, facial serial numbers, voice print (audio file) serial numbers and video frame serial numbers within predetermined live video and photographic image frames then randomly store the live web camera feed and streaming transmission data.

\* \* \* \* \*